US008263044B2

(12) United States Patent
Srinivas et al.

(10) Patent No.: US 8,263,044 B2
(45) Date of Patent: Sep. 11, 2012

(54) STILBENE LIKE COMPOUNDS AS NOVEL HDAC INHIBITORS

(75) Inventors: Akella Satya Surya Visweswara Srinivas, Chennai (IN); Urkalan Kaveri Balan, Chennai (IN); Narayana Swamy Punthalir, Chennai (IN); Rama Swamy Velmurugan, Chennai (IN); Sriram Rajagopal, Chennai (IN); Gaddam Om Reddy, Chennai (IN); Virendra Kachhadia, Chennai (IN)

(73) Assignee: Orchid Research Laboratories Limited, Tamil-Nadu (IN)

( * ) Notice: Subject to any disclaimer, the term of this patent is extended or adjusted under 35 U.S.C. 154(b) by 395 days.

(21) Appl. No.: 12/084,430

(22) PCT Filed: Nov. 6, 2006

(86) PCT No.: PCT/IB2006/003114
§ 371 (c)(1),
(2), (4) Date: Jun. 26, 2008

(87) PCT Pub. No.: WO2007/054776
PCT Pub. Date: May 18, 2007

(65) Prior Publication Data
US 2009/0136431 A1    May 28, 2009

(30) Foreign Application Priority Data
Nov. 10, 2005 (IN) .............. 1644/CHE/2005

(51) Int. Cl.
| A61K 9/12 | (2006.01) |
| A61K 31/427 | (2006.01) |
| A61K 31/4409 | (2006.01) |
| C07D 417/04 | (2006.01) |
| C07D 213/56 | (2006.01) |
| A61P 35/00 | (2006.01) |

(52) U.S. Cl. .......... 424/45; 435/375; 514/357; 514/365; 546/340; 548/204

(58) Field of Classification Search ........................ None
See application file for complete search history.

(56) References Cited

U.S. PATENT DOCUMENTS
5,369,108 A    11/1994    Breslow et al.
6,624,197 B1    9/2003    Nag et al.
2005/0038125 A1    2/2005    Smit et al.

FOREIGN PATENT DOCUMENTS
WO    WO 98/55449    12/1998

OTHER PUBLICATIONS

Andreeva et al, caplus an 2005:1281800.*
Hacks Chemical Dictionary, Fourth Edition, Julius Grant, 1972, p. 203.*
Chawla et al., "Challenges in Polymorphism of Pharmaceuticals", CRIPS vol. 5, No. 1, Jan.-Mar. 2004 (4 PAGES.*
Newman et al., "Solid-state analysis of the active pharmaceutical ingredient in drug products", DDT vol. 8, No. 19, Oct. 2003, p. 898-905.*
Stewart et al., caplus an 2006:823400.*
Tung et al., caplus an 1997:113367.*
Kono et al., caplus an 2002:378541.*
Numerof et al., Eur. Cytokine Netw, 16, 2005, 101-103.*
McLaughlin et al., Current Drug Targets—Inflammation & Allergy, 2004, 3, 213-219.*
Parkin et al., "Global Cancer Statistics," *Cancer Journal for Clinicians*, Mar./Apr. 2005, vol. 55, No. 2, pp. 74-108.
Hill, "Radiation effects on the respiratory system," *The British Institute of Radiology*, 2005, pp. 75-81.
Bharti et al., "Curcumin (Diferuloylmethane) Inhibits Constitutive and IL-6-Inducible STAT3 Phosphorylation in Human Multiple Myeloma Cells," *Journal of Immunology*, 2003, vol. 171, No. 7, pp. 3863-3871.
Vermal et al., "Jak family of kinases in cancer," *Cancer Metastasis Review*, 2003, vol. 22, No. 4, pp. 423-434 (Abstract Only).
Kerr et al., "Of JAKs, STATs, blind watchmakers, jeeps and trains," *FEBS Letters*, Apr. 28, 2003, vol. 546, pp. 1-5.
Catlett-Falcone et al., "Constitutive Activation of Stat3 Signaling Confers Resistance to Apoptosis in Human U266 Myeloma Cells," *Immunity*, Jan. 1999, vol. 10, pp. 105-115.
Alas et al., "Inhibition of Constitutive STAT3 Activity Sensitizes Resistant Non-Hodgkin's Lymphoma and Multiple Myeloma to Chemotherapeutic Drug-mediated Apoptosis," *Clinical Cancer Research*, Jan. 2003, vol. 9, pp. 316-326.

(Continued)

Primary Examiner — Sun Jae Loewe
(74) *Attorney, Agent, or Firm* — Oliff & Berridge, PLC

(57) ABSTRACT

The present invention relates to novel stilbene like compounds of the general formula (I), their derivatives, analogs, tautomeric forms, stereoisomers, polymorphs, hydrates, solvates, pharmaceutically acceptable salts and compositions, metabolites and prodrugs thereof. The present invention more particularly provides novel stilbene like compounds of the general formula (I). Also included is a method for treatment of cancer, psoriasis, proliferative conditions and conditions mediated by HDAC, in a mammal comprising administering an effective amount of a novel compound of formula (I) as described above.

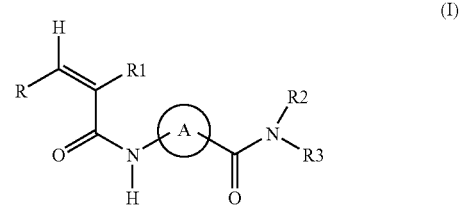

(I)

17 Claims, No Drawings

OTHER PUBLICATIONS

Burdelya et al., "Combination Therapy with AG-490 and Interleukin 12 Achieves Greater Antitumor Effects than Either Agent Alone," *Molecular Cancer Therapeutics*, 2002, vol. 1, No. 11, pp. 893-899.

Matter, Alex, "Tyrosine kinase inhibitors in cancer drug discovery," *International Symposium on Predictive Oncology and Intervention Strategies*, Paris, France, Feb. 9-12, 2002, in the section "Molecular Basis of Oncogenesis."

Klein et al., "Murine Anti-Interleukin-6 Monoclonal Antibody Therapy for a Patient With Plasma Cell Leukemia," *Blood*, Sep. 1, 1991, vol. 78, No. 5, pp. 1198-1204.

Lu et al., "High amounts of circulating interleukin (IL)-6 in the form of monomeric immune complexes during anti-IL-6 therapy. Towards a new methodology for measuring overall cytokine production in human in vivo," *European Journal of Immunology*, 1992, vol. 22, pp. 2819-2824 (Abstract Only).

Hallek et al., "Multiple Myeloma: Increasing Evidence for a Multistep Transformation Process," *Blood*, Jan. 1, 1998, vol. 91, No. 1, pp. 3-21.

Selvanayagam et al., "Alteration and abnormal expression of the c-myc oncogene in human multiple myeloma," *Blood*, Jan. 1988, vol. 71, No. 1, pp. 30-35.

Pettersson et al., "Expression of the bcl-2 gene in human multiple myeloma cell lines and normal plasma cells," *Blood*, Jan. 15, 1992, vol. 79, No. 2, pp. 495-502.

Hideshima et al., "Advances in biology of multiple myeloma: clinical applications," *Blood*, Aug. 1, 2004, vol. 104, No. 3, pp. 607-618.

Manickam et al., "Antihyperglycemic Activity of Phenolics from *Pterocarpus marsupium*," *Journal of Natural Products*, 1997, vol. 60, No. 6, pp. 609-610 (Abstract Only).

Marks et al., "Histone Deacetylase Inhibitors: Inducers of Differentiation or Apoptosis of Transformed Cells," *Journal of the National Cancer Institute*, Aug. 2, 2000, vol. 92, No. 15, pp. 1210-1216.

Wegener et al., "Abteilung fuer Molekulare Genetik and Praeparative Molekularbiologie," *Analytical Biochemistry*, Oct. 15, 2003, vol. 321, Issue 2, pp. 202-208 (Abstract Only).

* cited by examiner

STILBENE LIKE COMPOUNDS AS NOVEL HDAC INHIBITORS

FIELD OF THE INVENTION

The present invention relates to novel stilbene like compounds of the general formula (I), their derivatives, analogs, tautomeric forms, stereoisomers, polymorphs, hydrates, solvates, pharmaceutically acceptable salts and compositions metabolites and prodrugs thereof. The present invention more particularly provides novel, stilbene like compounds of the general formula (I).

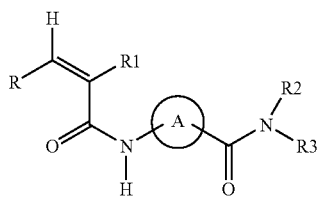

(I)

The present invention also provides a process for the preparation of the above said novel stilbene like compounds of the formula (I), their derivatives, analogs, stereoisomers, polymorphs, hydrates, solvates, their pharmaceutically acceptable salts and compositions metabolites and prodrugs thereof.

BACKGROUND OF THE INVENTION

The present invention relates to potentially pharmaceutical compositions and in particular to new molecules as active ingredients, that are used in particular as anticancer agents. Compounds of the general formula (I), or pharmaceutically acceptable salts thereof according to the present invention have an ability of inhibiting histone deacetylating enzyme and of inducing differentiation and are useful as therapeutic or ameliorating agent for diseases that are involved in cellular growth such as malignant tumors, autoimmune diseases, skin diseases, infections etc.

The novel stilbene like compounds (I) of the present invention are useful for the treatment cancer, which is one of the leading causes of death in the present society. A great deal of effort has been underway to treat various forms of cancer for decades and until recently. Chemoprevention of cancer is receiving its due share of attention.

Cancer may affect people at all ages, but risk tends to increase with age, due to the fact that DNA damage becomes more apparent in aging DNA. It is one of the principal causes of death in developed countries, more than 11 million people are diagnosed with cancer every year, and it is estimated that there will be 16 million new cases every year by 2020. Cancer causes 7 million deaths every year or 12.5% of deaths worldwide. Cancer is a leading cause of death worldwide particularly affecting major portion of people in industrialized world than in the non-industrialized world. From a total of 58 million deaths worldwide in 2005, cancer accounts for 7.6 million (or 13%) of all deaths. The main types of cancer leading to overall cancer mortality are Lung (1.3 million deaths/year), Stomach (almost 1 million deaths/year), Liver (662,000 deaths/year), Colon (655,000 deaths/year) and Breast (502,000 deaths/year). Deaths from cancer in the world are projected to continue rising, with an estimated 9 million people dying from cancer in 2015 and 11.4 million dying in 2030 (Parkin D et al, 2002)

Every cell constantly faces decisions. Should it divide? Or should it differentiate? Or should it die (Apoptosis)? Proper development and tissue homeostasis rely on the correct balance between division and apoptosis. Too much apoptosis leads to tissue atrophy such as in Alzheimer's disease. Too much proliferation or too little apoptosis leads to cancer. Cancer is a disease of multifactorial origin characterized by uncontrolled division of cells; when the cancer cell faces spatial restrictions, due to uncontrolled proliferation in an organ of the body, the ability of the cell to invade other distinct tissues occurs by a process defined as "Metastasis" the stage in which cancer cells are transported through the bloodstream or lymphatic system.

The most common treatment for easily accessible cancer is surgical removal of diseased tissues and radiation. The choice of treatment for in-accessible tumors is chemotherapy. Also chemotherapy is given as additional insurance for most cancer as it is difficult to access the extent of metastasis.

Most clinically revelant anticancer drugs currently used in the clinic, interfere with cell division and hence are not highly selective to cancer cells and there are potential chances, that chemotherapy can lead to secondary cancers in due course of time. Also the quality of life is hampered in the patients upon chemotherapy, hence there is an unmet medical need for treating cancer patients without affecting the quality of life. (Hill R P et al., 2005 & Kleinsmith, L J, 2006).

The cell cycle deregulation and the molecular basis of cancer cell growth has been thoroughly exploited in the recent years. Inhibition of signal transduction has become a viable and attractive avenue in biomedical cancer research based on the discovery of a large number of somatic mutations in many different types of cancer that lead to deregulated growth signal transduction and subsequent aberrant growth, invasion, tumor-derived angiogenesis and metastasis. Most of the non-cytotoxic drugs that have been recently developed include Protein kinase inhibitors such as Gleevec, Iressa and Tarceva, Tyrosine kinase inhibitors like Leflunomide. Glivec™ (STI571), is an inhibitor of the bcr-abl kinase and CML. PKI166, on the other hand, is a dual inhibitor of EGF receptor (HER 1) as well as erbB (HER 2). EGF-receptor and PTK787, potent inhibitors of VEGF-receptor 2 (KDR) are able to suppress tumor growth via suppression of tumor angiogenesis and also these agents have entered clinical trials in tumor patients (Alex Matter, M.D., 2002). These types of orally active and relatively well-tolerated compounds can be used in the clinics; either as single agents or in combination with other well established cytotoxic agents.

Cytokines play an important role in the communication between cells of multicellular organisms. Early studies indicate that B cells lineage tend to secrete IL6 in response to host immune defense mechanisms, but in recent decades studies have indicated elevated levels of IL6 in various cancer phenotypes. IL6 promotes survival and proliferation of certain cancerous cell lines through the phosphorylation of STAT3 (Bharti et al., Verma et al., Kerr et al.). Inhibitors of Jak/Stat pathway likely represent potential therapeutic targets for cancer (Catlett Falcone et al., 1999; Alas and Bonavida, 2003; Burdelya et al., 2002)

IL6 has been found to be a growth factor for multiple myeloma cells; anti IL6 antibodies were shown to block myeloma cell proliferation in a leukemic patients (Lkein et al., Blood, 78, (5), pp 1198-1204, 1991 and Lu et al., Eur. J. Immunol., 22. 2819-24, 1992). A need exists for a compound that blocks IL6 mediated Stat3 activation at lower concentration and suppresses expression of proto-oncogenes like c-myc, which is over expressed, rearranged or mutated in many malignancies (Hallek et al., 1998; Selvanayagam et al., 1988; Jemberg-Wiklund et al., 1992; Kuehl et al., 1997).

Elevation of inflammatory cytokine levels, particularly IL-6 and TNF-α also appears to be associated with the Cancer-related cachexia, a syndrome involving loss of adipose and skeletal muscle tissue, and one that is not responsive to increased caloric intake. Cachexia may also be related to the role of acute phase proteins. The acute phase response and production of acute phase proteins (e.g., C-reactive protein CRP) are mediated by IL-6. Studies correlate elevated levels of IL-6 elevate acute phase proteins, which, interestingly, are also associated with increased weight loss and decreased survival. Thus, with elevated IL-6 levels, amino acid metabolism is directed away from peripheral tissues to the liver for production of acute phase proteins. This in turn leads to muscle wasting, which is a component of cachexia. Accordingly, the cytokine-induced acute phase response may be a primary component of cancer-related cachexia. Moreover, diminishing or blocking IL-6 activity in animal models attenuates cachexia, further demonstrating the essential role IL-6 plays in the development of this syndrome.

Resveratol, a representation of hydroxystilbene, is a plytoalexin present in grapes and other food products and has received special attention. It is known to possess a variety of biological significances such as cancer chemo-preventive activity, anti-inflammatory activity through inhibition of cyclooxygenase. It also inhibits arachidonate release, MAPK activation, protein kinase and degruanulation of mast cells and is a known antioxidant having anti-cancer as well as anti-diabetic activity. It has been suggested as a potential cancer chemo-preventive agent based on its striking inhibitory effects on cellular events associated with cancer initiation, promotion, and progression. This triphenolic stilbene has also displayed in vitro growth inhibition in a number of human cancer cell lines.

Hypoglycemic activity of a naturally occurring pterostilbene, trans-1-(3,5-dimethoxyphenyl-2-(4-hydroxyphenyl) ethylene, and its isolation from the heartwood of pterocarpus marsupium have been reported by Manickam et al, J. Natu. Prod., 1997, 60:609-610.

NF-kB that plays an important role in INOS (inducible nitric oxide syntheses) expression is one of the targets of various potential anti-inflammatory agents including Resveratol.

The first isolation of histone deacetylase was described in 1964 from crude nuclear extracts of cells, but the molecular characterization of isoforms of the enzyme has been achieved only recently. Inhibitors of histone deacetylase (HDAC's) are zinc hydrolase's responsible for the deacetylation of N-acetyl lysine residues of histone and nonhistone protein substrates. Human HDAC's are classified into two distinct classes, the HDAC's and sirtuins. The HDAC's are devised into two subclasses based on their similarity to yeast histone deacetylases, RPD 3 (class I includes HDAC 1, 2, 3, 8, and 11) and Hda 1 (class II includes HDAC 4, 6, 7, 9, and 10). All of the HDAC's have a highly conserved zinc dependent catalytic domain. There is growing evidence that the acetylation state of proteins and thus the HDAC enzyme family plays a crucial role in the modulation of a number of biological processes, including transcription and cell cycle.

Transcriptional regulation is a major event in cell differentiation, proliferation and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription factors to their target DNA regiments. Nucleosomal integrity is regulated by the acetylating status of the core histone, with the result being permissiveness to transcription. The acetylating status of the histone is governed by the balance of activities of the histone acetyl transferase (HAT) and histone deacetylase (HDAC). Recently HDAC inhibitors have been found to arrest growth and apoptosis in several types of cancer cells, including colon cancer, t-cell lymphoma and erythroleukemic cells.

Given that apoptosis is a crucial factor for cancer progression, HDAC inhibitors are promising reagents for cancer therapy as effective inducers of apoptosis.

Several structural classes of HDAC inhibitors have been identified and are reviewed in Marks, P. A. et al., J. Natl. Cancer Inst., 92, (2000), 1210-1215. More specifically WO 98/55449 and U.S. Pat. No. 5,369,108 report alkanoyl hydroxamates with HDAC inhibitory activity.

Few prior art references, which disclose the closest compounds, are given here:

I). U.S. Pat. No. 6,624,197 B1 discloses a class of novel diphenylethylenes of the formula I,

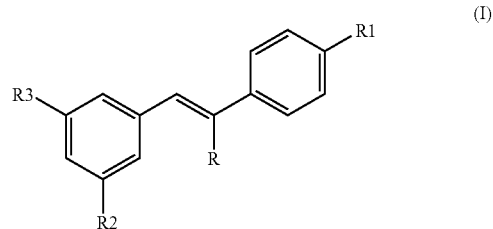

wherein R is hydrogen or —$CO_2Z$, Z is hydrogen or a cation; and $R_1$, $R_2$ and $R_3$ are each independently H, —OH or —$OR_4$, wherein $R_4$ is linear or branched alkyl of 1-12 carbon atoms; with the condition that when R is hydrogen and $R_2$=$R_3$=— OMe, then $R_1$ is not —OH. The configuration around the double bond may be E/Z.

A novel class of styrenes of the formula II is also provided,

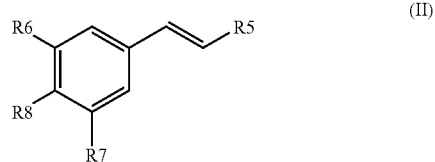

wherein $R_5$ is hydrogen or methyl; $R_6$ and $R_7$ are independently hydrogen or OMe; $R_8$ is hydrogen or hydroxy. The configuration around the double bond may be E/Z. Pharmaceutical compositions of compounds of the formula I or II are provided for the treatment of diabetes comprising of therapeutically effective amount of the compounds in a physiologically acceptable carrier. A method of treating diabetes is also provided comprising a step of orally administering to a subject suffering from a diabetic condition a therapeutically effective amount of a compound of formula I or II.

II). US 20050038125 discloses the invention related to a method for the treatment and/or prevention of disorders with elevated $PGE_2$ (such as arthritis, fybromyalgia and pain) and/ or $LTB_4$ levels (such as asthma, allergy, arthritis, fybromyalgia and inflammation), comprising administering to a mammal an effective amount of pterostilbene component (PS component), a pharmaceutically acceptable salt of PS component or a precursor of PS component, wherein the PS component has the formula 1 as shown below

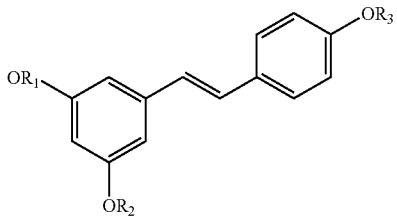

in which $R_1$, $R_2$ and $R_3$ are independently selected from hydrogen, $C_{1-50}$ hydrocarbyl, $C_{1-50}$ so substituted hydrocarbyl, $C_{1-50}$ heterohydrocarbyl, $C_{1-50}$ substituted heterohydrocarbyl; and wherein at least one of $R_1$ and $R_2$ is not hydrogen

OBJECTIVE OF THE INVENTION

Due to unmet medical needs and also as all of us know, cancer is one of the leading causes of death in the present society, we focused our attention to identify novel small molecule anticancer agents, particularly focusing on HDAC inhibitors. Our sustained efforts have resulted in novel anticancer agents of the formula (I). Histone acetylation and deacetylation play an essential role in modifying chromatin structure and regulating gene expression in eukaryotic cells. Hyper acetylated histones are generally found in transcriptionally active genes and in transcriptionally silent regions of the genome. Key enzymes, which modify histone proteins and thereby regulate gene expression, are histone acetyl transferases (HATs) and histone deacetylases (HDACs). Compounds able to inhibit HDAC activity i.e. HDAC inhibitors such as Trichostatin A (TSA), Trapoxin (TPX), Suberoylanilide hydroxamic acid (SAHA), Sodium butyrate (NaB), Sodium valproate (VPA), Cyclic hydroxamic acid containing peptides (CHAPs), Depsipeptide FK-228 and MS-275 can de-repress these genes, resulting in antiproliferative effects in vitro and anti tumor effects in vivo.

SUMMARY OF THE INVENTION

The present invention relates to novel stilbene like compounds of the general formula (I),

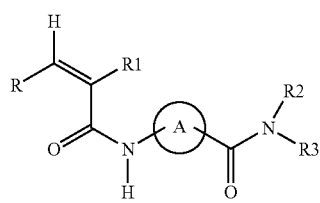

their derivatives, analogs, tautomeric forms, stereoisomers, polymorphs, solvates, pharmaceutically acceptable salts and compositions, metabolites and prodrugs thereof, wherein A represents —$CH_2)_n$ which may be optionally substituted or unsubstituted by groups selected from aryl, aralkyl, heteroaryl and the like, which may be further substituted; R and $R_1$ represent optionally substituted or unsubstituted groups selected from aryl, heteroaryl and benzo fused heteroaryl; wherein $R_2$ and $R_3$ represent optionally substituted or unsubstituted groups which may be same or different and represents hydrogen, hydroxy, alkyl, alkoxy, benzyloxy acetyl, cycloalkyl, aryl, heterocyclyl, heteroaryl, benzofused heteroaryl; n is an integer in the range of 1 to 8.

DETAILED DESCRIPTION OF THE INVENTION

The present invention relates to novel stilbene like compounds of the general formula (I),

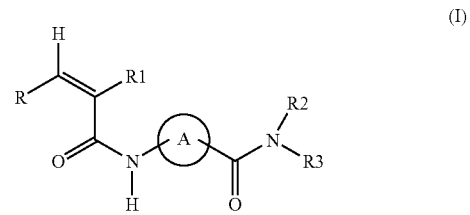

their derivatives, analogs, tautomeric forms, stereoisomers, polymorphs, solvates, pharmaceutically acceptable salts and compositions metabolites and prodrugs thereof, wherein A represents —$CH_2)_n$ which may be optionally substituted or unsubstituted by groups selected from aryl, arylalkyl, heteroaryl and the like, which may be further substituted, the substitutents may be selected from hydroxy, halogen and the like.

Suitable groups represented by R and $R_1$ represent aryl groups such as phenyl, naphthyl and the like which may be substituted; heteroaryl groups such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl and the like, which may be substituted and benzo fused heteroaryl groups such as quinoline, quinoxaline, acridine, phenazine and the like which may be substituted.

Suitable groups represented by $R_2$ and $R_3$ may be selected from hydrogen, hydroxyl, substituted or unsubstituted groups selected from, linear or branched ($C_1$-$C_4$) alkyl groups such as methyl, ethyl, n-propyl, isopropyl, n-butyl, isobutyl, t-butyl and the like, alkoxy groups such as methoxy, ethoxy, propoxy, n-butoxy, isobutoxy, t-butoxy and the like; benzyloxy; acetyl; benzyloxy acetyl; cycloalkyl groups such as cyclohexyl, cycloheptyl, cyclooctyl and the like; aryl groups such as phenyl, naphthyl and the like; heterocyclyl groups such as pyrrolidinyl, thiazolidinyl, oxazolidinyl, morpholinyl, thiomorpholinyl, piperidinyl, piperazinyl, and the like; heteroaryl groups such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl and the like; benzo fused heteroaryl groups such as quinoline, quinoxaline, acridine, phenazine, benzothiazole and the like.

n is an integer in the range of 1 to 8.

When the groups R, $R_1$, $R_2$ and $R_3$ are substituted, the substituents (which may be one or more) may be selected from halogens (fluorine, chlorine, bromine, iodine), hydroxy, nitro, cyano, azido, nitroso, amino, hydrazine, hydroxamate, formyl, alkyl, haloalkyl, haloalkoxy, cycloalkyl, aryl, benzyl, alkoxy, aryloxy, acyl, acyloxy, acyloxyacyl, heterocyclyl, heteroaryl, monoalkylamino, dialkylamino, acylamino, alkoxycarbonyl, aryloxycarbonyl such as methoxy carbonyl, ethoxycarbonyl and the like; alkylsulfonyl, arylsulfonyl, alkylsulfinyl, arylsulfinyl, thioalkyl, arylthio, sulfamoyl, alkoxyalkyl groups and carboxylic acids and its derivatives like esters, hydroxamic acid and hydroxamate these groups may be further substituted by groups such as hydroxy.

Furthermore, whenever the groups R, $R_1$, $R_2$ and $R_3$ represent substituted or unsubstituted 5 to 10 membered ring systems, the rings may be monocyclic or bicyclic, saturated or partially saturated or aromatic containing 1 to 4 heteroatoms selected from O, S and N.

DEFINITIONS

As used throughout the specification and the appended claims the following terms have the following meanings:

The term analog includes a compound, which differs from the parent structure by one or more C, N, O or S atoms. Hence, a compound in which one of the N atoms in the parent structure is replaced by an S atom is an analog of the former.

The term stereoisomer includes isomers that differ from one another in the way the atoms are arranged in space, but whose chemical formulas and structures are otherwise identical. Stereoisomers include enantiomers and diastereoisomers.

The term tautomers include readily interconvertible isomeric forms of a compound in equilibrium. The enol-keto tautomerism is an example.

The term polymorphs include crystallographically distinct forms of compounds with chemically identical structures.

The term pharmaceutically acceptable solvates includes combinations of solvent molecules with molecules or ions of the solute compound.

The term derivative refers to a compound obtained from a compound according to formula (I), an analog, tautomeric form, stereoisomer, polymorph, hydrate, pharmaceutically acceptable salt or pharmaceutically acceptable solvate thereof, by a simple chemical process converting one or more functional groups, such as, by oxidation, hydrogenation, alkylation, esterification, halogenation, and the like.

Pharmaceutically acceptable salts forming part of this invention include base addition salts such as alkali metal salts like Li, Na, and K salts, alkaline earth metal salts like Ca and Mg, salts of organic bases such as lysine, arginine, guanidine, diethanolamine, α-phenylethylamine, benzylamine, piperidine, morpholine, pyridine, hydroxyethylpyrrolidine, hydroxyethylpiperidine, choline and the like, ammonium or substituted ammonium salts, aluminum salts. Salts also include amino acid salts such as glycine, alanine, cystine, cysteine, lysine, arginine, phenylalanine, guanidine etc. Salts may include acid addition salts where appropriate which are sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like.

Pharmaceutically acceptable solvates may be hydrates or comprising of other solvents of crystallization such as alcohols.

Particularly useful compounds according to the present invention include:

1. (2Z)-3-(3,5-Dimethoxyphenyl)-2-(4-fluorophenyl)-N-[6-(2-hydroxybenzyl amine)-6-oxohexyl]acrylamide;
2. (2Z)-3-(3,5-Dimethoxyphenyl)-2-(4-fluorophenyl)-N-[6-(3-hydroxybenzyl amine)-6-oxohexyl]acrylamide;
3. (2Z)-3-(3,5-Dimethoxyphenyl)-2-(4-fluorophenyl)-N-[6-(hydroxyamino)-6-oxohexyl]acrylamide;
4. (2Z)-3-(3,5-Dimethoxyphenyl)-2-(4-hydroxyphenyl)-N-[6-(2-aminobenzyl amine)-6-oxohexyl]acrylamide;
5. (2Z)-3-(3,5-Dimethoxyphenyl)-2-(4-hydroxyphenyl)-N-[6-(2-hydroxybenzyl amine)-6-oxohexyl]acrylamide;
6. (2Z)-3-(3,4,5-Trimethoxyphenyl)-2-(4-hydroxyphenyl)-N-[6-(2-hydroxybenzyl amine)-6-oxohexyl]acrylamide;
7. (2Z)-3-(3,4,5-Trimethoxyphenyl)-2-(4-hydroxyphenyl)-N-[6-(N,O dimethyl amine)-6-oxohexyl]acrylamide;
8. [(2Z)-3-(4-Methyl-1,3-thiazol-5-yl)-2-(2-thienyl))-N-[6-(hydroxyamino)-6-oxohexyl]acrylamide;
9. (2Z)-3-(3,5-Dimethoxyphenyl)-2-(4-nitrophenyl)-N-[6-(hydroxyamino)-6-oxohexyl]acrylamide;
10. (2Z)-3-(3-Chloro,4-fluorophenyl)-2-(4-fluorophenyl)-N-[6-(hydroxyamino)-6-oxohexyl]acrylamide;
11. (2Z)-3-(3,5-dimethoxyphenyl)-2-(4-hydroxyphenyl)-N-[6-(hydroxyamino)-6-oxohexyl]acrylamide;
12. (2Z)-3-(4-Methyl-1,3-thiazol-5-yl)-2-(4-chlorophenyl)-N-[6-(hydroxyamino)-6-oxohexyl]acrylamide;
13. (2Z)-3-(5-Bromo-2-thienyl)-2-(4-bromophenyl)-N-[6-(hydroxyamino)-6-oxohexyl]acrylamide;
14. (2Z)-3-(4-Pyridine)-2-(4-fluorophenyl)-N-[6-(hydroxyamino)-6-oxohexyl]acrylamide;
15. (2Z)-3-(4-Pyridine)-2-(4-fluorophenyl)-N-[6-(4-hydroxy-2-nitrobenzylamine)-6-oxohexyl]acrylamide;
16. (2Z)-3-(4-Thiomethylphenyl)-2-(4-fluorophenyl)-N-[6-(hydroxyamine)-6-oxohexyl]acrylamide;
17. (2Z)-3-(4-Thiomethylphenyl)-2-(4-fluorophenyl)-N-[6-(5-nitro-2-thiazoleamine)-6-oxohexyl]acrylamide;
18. (2Z)-3-(4-Thiomethylphenyl)-2-(4-fluorophenyl)-N-[6-(N,O dimethylamine)-6-oxohexyl]acrylamide;
19. (2Z)-3-(4-Thiomethylphenyl)-2-(4-fluorophenyl)-N-[6-(5-methyl-2-benzo thiazoleamine)-6-oxohexyl]acrylamide;
20. (2Z)-3-(4-Thiomethylphenyl)-2-(4-fluorophenyl)-N-[6-(2-thiazoleamine)-6-oxohexyl]acrylamide;
21. (2Z)-3-(3,4-Difluorophenyl)-2-(4-fluorophenyl)-N-[6-(2-thiazoleamine)-6-oxohexyl]acrylamide;
22. (2Z)-3-(4-Fluoro-3-trifluoromethyl-phenyl)-2-(4-trifluoromethylphenyl)-N-[6-(hydroxyamino)-6-oxohexyl]acrylamide;
23. (2Z)-3-(4-Methylthiazol-5-yl)-2-(4-bromophenyl)-N-[6-(hydroxyamino)-6-oxohexyl]acrylamide;
24. (2Z)-3-(4-Fluoro-3-trifluoromethylphenyl)-2-(4-nitrophenyl)-N-[6-(hydroxyamino)-6-oxohexyl]acrylamide;
25. (2Z)-3-(2,3,5-Trifluorophenyl)-2-(thiophene-2-yl)-N-[6-(hydroxyamino)-6-oxohexyl]acrylamide;
26. (2Z)-3-(4-Methylthiazol-5-yl)-2-(4-trifluoromethylphenyl)-N-[6-(hydroxyamino)-6-oxohexyl]acrylamide;
27. (2Z)-3-(2,3,5-Trifluorophenyl)-2-(4-nitrophenyl)-N-[6-(hydroxyamino)-6-oxohexyl]acrylamide;
28. (2Z)-3-(3-Chlorophenyl)-2-(4-methoxyphenyl)-N-[6-(hydroxyamino)-6-oxohexyl]acrylamide;
29. (2Z)-3-(4-Methoxyphenyl)-2-(phenyl)-N-[6-(hydroxyamino)-6-oxohexyl]acrylamide;
30. (2Z)-3-(2-Nitrophenyl)-2-(4-chlorophenyl)-N-[6-(hydroxyamino)-6-oxohexyl]acrylamide;
31. (2Z)-3-(2-Chloro-4-fluorophenyl)-2-(phenyl)-N-[6-(hydroxyamino)-6-oxohexyl]acrylamide;
32. (2Z)-3-(2,3,4-Trimethoxyphenyl)-2-(4-hydroxyphenyl)-N-[6-(hydroxyamino)-6-oxohexyl]acrylamide;
33. (2Z)-3-(3,5-Dimethoxyphenyl)-2-(4-fluorophenyl)-N-[6-(hydroxyamino)-6-oxohexyl]acrylamide;
34. (2Z)-3-(3,4-Difluorophenyl)-2-(4-fluorophenyl)-N-[6-(hydroxyamino)-6-oxohexyl]acrylamide;
35. (2Z)-3-(3,4-Difluorophenyl)-2-(4-fluorophenyl)-N-[6-(N,O dimethyl hydroxyamino)-6-oxohexyl]acrylamide;
36. (2Z)-3-(3,4-Difluorophenyl)-2-(4-fluorophenyl)-N-[6-(amino thiazol-2-yl)-6-oxohexyl]acrylamide;
37. (2Z)-3-(5-Chloro-2-furyl)-2-(4-fluorophenyl)-N-[6-(hydroxyamino)-6-oxohexyl]acrylamide;

38. (2Z)-3-(4-Thiomethylphenyl)-2-(4-trifluoromethylphenyl)-N-[6-(hydroxyamino)-6-oxohexyl]acrylamide;
39. (2Z)-3-(Thiazol-2-yl)-2-(4-trifluoromethylphenyl)-N-[6-(hydroxyamino)-6-oxohexyl]acrylamide;
40. (2Z)-3-(2,3,6-Trifluorophenyl)-2-(4-methoxyphenyl)-N-[6-(hydroxyamino)-6-oxohexyl]acrylamide;
41. (2Z)-3-(4-Thiomethylphenyl)-2-(4-nitrophenyl)-N-[6-(hydroxyamino)-6-oxohexyl]acrylamide;
42. (2Z)-3-(3-Chloro-4-fluorophenyl)-2-(4-hydroxyphenyl)-N-[6-(hydroxyamino)-6-oxohexyl]acrylamide;
43. (2Z)-3-(4-Thiomethylphenyl)-2-(thiophene-2-yl)-N-[6-(hydroxyamino)-6-oxohexyl]acrylamide;
44. (2Z)-3-(5-Chlorothiophen-2-yl)-2-(4-fluorophenyl)-N-[6-(hydroxyamino)-6-oxohexyl]acrylamide;
45. (2Z)-3-(4-Fluoro-3-methylphenyl)-2-(4-fluorophenyl)-N-[6-(hydroxyamino)-6-oxohexyl]acrylamide;
46. (2Z)-3-(4-Hydroxy-3-methoxyphenyl)-2-(4-fluorophenyl)-N-[6-(hydroxyamino)-6-oxohexyl]acrylamide;
47. (2Z)-3-(4-Trifluoromethylphenyl)-2-(4-fluorophenyl)-N-[6-(hydroxyamino)-6-oxohexyl]acrylamide;
48. (2Z)-3-(3,4,5-Trimethoxyphenyl)-2-(4 fluorophenyl)-N-[6-(hydroxyamino)-6-oxohexyl]acrylamide;
49. N-[4-(hydroxyamino)-4-oxobutyl]-6-{[(2Z)-3-(3,5 dimethoxyphenyl)-2-(4 nitrophenyl)-acrylamide]}hexanamide;
50. (2Z)-3-(3,4,5-Trimethoxyphenyl)-2-(4-methoxyphenyl)-N-[6-(hydroxyamino)-6-oxohexyl]acrylamide;
51. (2Z)-3-(4-Thiomethylphenyl)-2-(4-fluorophenyl)-N-[6-(O-benzyl hydroxyamino)-6-oxohexyl]acrylamide;
52. N-Aetyl-6-{[(2Z)-3-(4-thiomethylphenyl)-2-(4-fluorophenyl)-acrylamide]}-N-hydroxyhexanamide;
53. N-Acetyl-6-{[(2Z)-3-(5-chloro-2-furyl)-2-(4-fluorophenyl)-acrylamide]}-N-hydroxyhexanamide;
54. N-Hydroxy-2-{[(2Z)-3-(4-thiomethylphenyl)-2-(4-fluorophenyl)-acrylamide]-6-oxohexyl]amino}-3-(4-hydroxyphenyl)propanamide;
55. Methyl-2-{[(2Z)-3-(2,3,5,6 tetrafluoro-4-methoxyphenyl)-2-(4-fluorophenyl)-acrylamide]6-oxohexyl]amino}-3-(4-hydroxyphenyl)propanoate;
56. N-Hydroxy-2-{[(2Z)-3-(2,3,5,6 tetrafluoro-4-methoxyphenyl)-2-(4-fluoro phenyl)-acrylamide]6-oxohexyl]amino}-3-(4-hydroxyphenyl)propanamide;
57. Methyl-2-{[(2Z)-3-(3,4 difluorophenyl)-2-(4-fluorophenyl)-acrylamide]6-oxohexyl]amino}-3-(4-hydroxyphenyl)propanoate;
58. N-hydroxy-2-{[(2Z)-3-(3,4 difluorophenyl)-2-(4-fluorophenyl)-acrylamide]6-oxohexyl]amino}-3-(4-hydroxyphenyl)propanamide;
59. (2Z)—N-(1-(4-hydroxybenzyl)-2-{[4-(hydroxyamino)-4-oxobutyl]amino}-2-oxoethyl)-3-(4-fluoro-3-trifluoro methylphenyl)-2-(4-nitrophenyl)-acrylamide;
60. (2Z)—N-[2-(hydroxyamino)-1-(4-hydroxybenzyl)-2-oxoethyl]-3-(4-fluoro-3-trifluoromethylphenyl)-2-(4-nitrophenyl)-acrylamide;
61. N-Hydroxy-2-{[(2Z)-3-(3,4 dimethoxyphenyl)-2-(4-fluorophenyl)-acrylamide]6-oxohexyl]amino}-3-(4-hydroxyphenyl)propanamide;
62. (2Z)—N-[2-(hydroxyamino)-1-(4-hydroxybenzyl)-2-oxoethyl]-3-(4-methyl thiazol-5-yl)-2-(thiophen-2-yl)-acrylamide;
63. (2Z)—N-[2-(Hydroxyamino)-1-(4-hydroxybenzyl)-2-oxoethyl]-3-(4 methoxy phenyl)-2-(phenyl)-acrylamide;
64. (2Z)—N-[2-(hydroxyamino)-1-(4-hydroxybenzyl)-2-oxoethyl]-3-(3,5 dimethoxyphenyl)-2-(4-hydroxyphenyl)-acrylamide and According to another feature of the present invention, there is provided a process as shown in the following scheme, for the preparation of compounds of the formula (I), wherein all the groups are as defined earlier.

A) By condensing the compound of formula (1a) and the compound of formula (1b) with Ac₂O to yield a compound of formula (1c), wherein R and R₁, are as defined earlier.

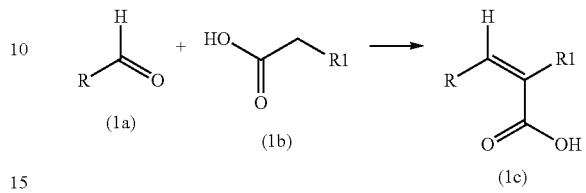

B) By reacting the compound of the formula (1c) with an acid activating agent such as BOP, HOBT and the like in the presence of the respective 5-aminocaproic methyl ester to yield the compound of the general formula (1d) wherein R and R₁ are as defined earlier.

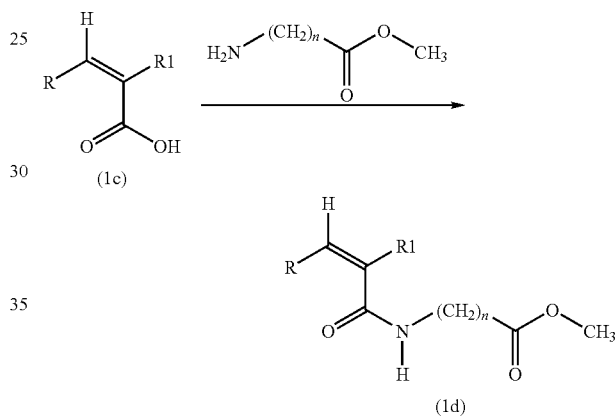

C) By reacting the compound of formula (1d) with a suitable base like LiOH, NaOH and the like to yield the compound of the general formula (1e) wherein R and R₁ are as defined earlier.

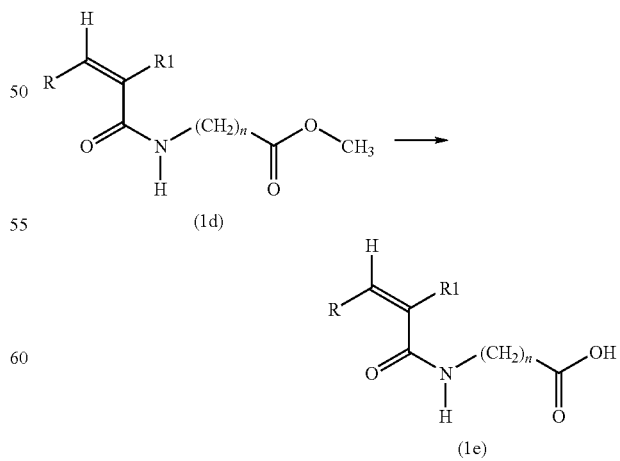

D) By reacting the compound of formula (1e) with an acid activating agent such as BOP, HOBT and the like in the presence of the respective amine $HNR_2R_3$ to yield the compound of the general formula (I) wherein R, $R_1$, $R_2$ and $R_3$ are as defined earlier.

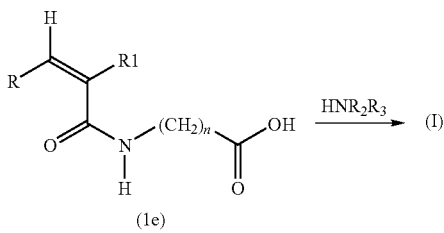

(1e)

The compound of the general formula (I) is prepared by the following procedure:

Step (I): Condensation of the compound of the formula (1a) and (1b) with TEA in the presence of a solvent such as $Ac_2O$, and a base such as triethylamine, diethylamine, pyridine, DMAP and the like, afforded the compound of the formula (1c), wherein R and $R_1$ are as defined earlier.

Step (II): Condensation of the compound of the formula (1c) with an acid activating agent such as BOP, HOBT and the like in the presence of the respective 5-aminocaproic methyl ester and base such as triethylamine, diethyl amine, pyridine, DMAP and like, yielded the compound of the general formula (1d), wherein R and $R_1$ are as defined earlier.

Step (III): Reaction of the compound of the formula (1d) with a suitable base like LiOH, NaOH and the like, yielded the compound of the general formula (1e), wherein R and $R_1$ are as defined earlier Step (IV): Condensation of the compound of the formula (1e) with an acid activating agent such as BOP, HOBT and the like in the presence of the respective amine $HNR_2R_3$, and base such as triethylamine, diethylamine, pyridine, DMAP and the like, yielded the compound of the general formula (I), wherein R, $R_1$, $R_2$ and $R_3$ are as defined earlier It is appreciated that in any of the above-mentioned reactions, any reactive group in the substrate molecule may be protected according to conventional chemical practice. Suitable protecting groups in any of the above-mentioned reactions are those used conventionally in the art. The methods of formation and removal of such protecting groups are those conventional methods appropriate to the molecule being protected. Protecting groups are removed under conditions, which will not affect the remaining portion of the molecule.

The pharmaceutically acceptable salts are prepared by reacting the compound of formula (I) with 1 to 4 equivalents of a base such as sodium hydroxide, sodium methoxide, sodium hydride, potassium t-butoxide, and calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

It should be noted that compounds of the invention may contain groups that may exist in tautomeric forms, and though one form is named, described, displayed and/or claimed herein, all the tauomeric forms are intended to be inherently included in such name, description, display and/or claim.

The stereoisomers of the compounds can also be made by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or by using chiral bases such as brucine, cinchona alkaloids, their derivatives and the like. Commonly used methods are compiled by Jaques et al in "Enantiomers, Racemates and Resolution" (Wiley Interscience, 1981).

Prodrugs of the compounds of formula (I) are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art.

Various polymorphs of the compounds of the general formula (I), forming part of this invention may be prepared by crystallization of the compounds of formula (I) under different conditions. For example, using different commonly used solvents, or their mixtures for recrystallization; crystallizations at different temperatures; various modes of cooling, ranging from very fast to very slow cooling during crystallizations. Heating or melting the compounds followed by cooling gradually or immediately, one can also obtain polymorphs. The presence of polymorphs may be determined by solid probe NMR spectroscopy, IR spectroscopy, differential scanning calorimetry and powder X-ray diffraction or other such techniques.

The present invention also provides a pharmaceutical composition, containing one or more of the compounds of the general formula (I) as defined above, their derivatives, analogs, tautomeric forms, stereoisomers, polymorphs, hydrates, metabolites, prodrugs, pharmaceutically acceptable salts, and pharmaceutically acceptable solvates in combination with the usual pharmaceutically employed carriers, diluents and the like, useful for the treatment and/or prevention of cancer, psoriasis, proliferative conditions, conditions mediated by HDAC and diseases involved in cellular growth such as malignant tumors, autoimmune diseases, skin diseases and infections.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. The amount of the active ingredient in the composition may be less than 70% by weight. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical compositions of the present invention are effective in treating and/or preventing cancer, psoriasis, proliferative conditions, conditions mediated by HDAC and diseases involved in cellular growth such as malignant tumors, autoimmune diseases, skin diseases and infections. Generally, the effective dose for treating a particular condition in a patient may be readily determined and adjusted by the physician during treatment to alleviate the symptoms or indications of the condition or disease. Generally, a daily dose of active compound in the range of about 0.01 to 1000 mg/kg of body weight is appropriate for administration to obtain effective results. The daily dose may be administered in a single dose or divided into several doses. In some cases, depending upon the individual response, it may be necessary to deviate upwards or downwards from the initially prescribed daily dose. Typical pharmaceutical preparations normally contain from about 0.2 to about 500 mg of active compound of formula I and/or its pharmaceutically active salts or solvates per dose.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition. Thus compounds of the present invention can be used in the treatment of cancer, psoriasis, as a monotherapy, or also in combination of these HDAC inhibitors with other clinically relevant cytotoxic agents or non-cytotoxic agents.

The term "therapeutically effective amount" or "effective amount" refers to that amount of a compound or mixture of compounds of formula (I) that is sufficient to effect treatment, as defined below, when administered alone or in combination with other therapies to an animal in need of such treatment.

The term "animal" as used herein is meant to include all mammals, and in particular humans. Such animals are also referred to herein as subjects or patients in need of treatment. The therapeutically effective amount will vary depending upon the subject and disease condition being treated, the weight and age of the subject, the severity of the disease condition, the particular compound of formula (I) chosen, the dosing regimen to be followed, timing of administration, the manner of administration and the like, all of which can readily be determined by one of ordinary skill in the art.

The term "treatment" or "treating" means any treatment of a disease in a mammal, including:
a) Preventing the disease, that is, causing the clinical symptoms of the disease not to develop;
b) Inhibiting the disease, that is, slowing or arresting the development of clinical symptoms; and/or
c) Relieving the disease, that is, causing the regression of clinical symptoms.

From the foregoing description, one skilled in the art can easily ascertain the essential characteristics of this invention, and without departing from the spirit and scope thereof, can make various changes and modifications of the invention to adapt it to various usages and conditions.

The present invention is provided by the examples given below, which are provided by the way of illustration only, and should not be considered to limit the scope of the invention. Variation and changes, which are obvious to one skilled in the art, are intended to be within the scope and nature of the invention, which are defined in the appended claims.

EXAMPLE 1

Synthesis of (2Z)-3-(3,5-Dimethoxyphenyl)-2-(4-fluorophenyl)-N-[6-(hydroxyamino)-6-oxohexyl] acrylamide

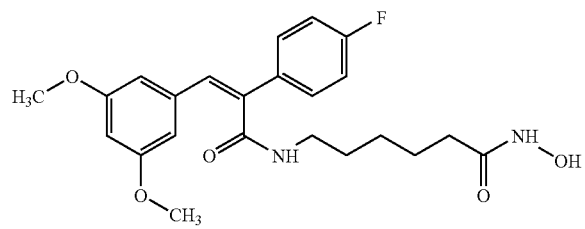

Stage 1

Synthesis of (2Z)-3-(3,5-Dimethoxyphenyl)-2-(4-fluorophenyl)acrylic Acid

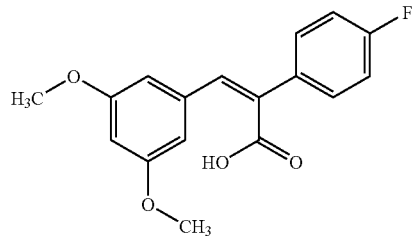

A mixture of 4-fluorophenyl acetic acid (0.928 g, 6.02 mmol), 3,5 dimethoxybenzaldehyde (1 g, 6.02 mmole), $Ac_2O$ (1 ml) and triethylamine (0.5 ml) was heated at 100° C. for 12 hours. Upon completion (as monitored by TLC using hexane-ethyl acetate (3:2), the reaction mixture was cooled to room temperature and concentrated HCL (5 ml) was added. The precipitate was dissolved in $CH_2Cl_2$ (100 ml), washed with 10% aqueous NaOH (3×50 ml) and the basic solution was acidified (PH-1) with concentrated HCL. After stirring, the precipitate was collected and dried to get the product (1.5 g, 82.87%).

Stage 2

Synthesis of Methyl 6-{[(2Z)-3-(3,5-Dimethoxyphenyl)-2-(4-fluorophenyl)prop-2-enoyl]amino}hexonate

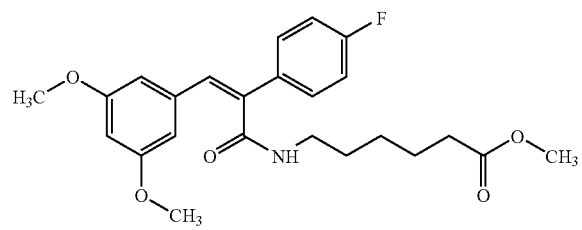

To a suspension of (2Z)-3-(3,5-dimethoxyphenyl)-2-(4-fluorophenyl)acrylic acid (1 g, 3.31 mmole) in THF was added 5-aminocaproic acid methyl ester (576 mg, 3.97 mmol), BOP reagent (1.75 g, 3.97 mmol), and HOBT (536 mg, 3.97 mmol). DIPEA (2.5 ml, 9.93 mmol) was added dropwise with constant stirring to the above and the reaction mixture was stirred at room temperature overnight. Subsequently the reaction mixture was evaporated to dryness. The residue was dissolved in ethyl acetate and washed successively with 1N HCL (3×50 ml), saturated NaHCO$_3$ (3×50 ml) and brine solution (3×50 ml). The organic layer was dried over Na$_2$SO$_4$ and concentrated to give the pure compound (1.100 g, 77.46%).

Stage 3

Synthesis of 6-{[(2Z)-3-(3,5-Dimethoxyphenyl)-2-(4-fluorophenyl)prop-2-enoyl]amino}hexanoic Acid

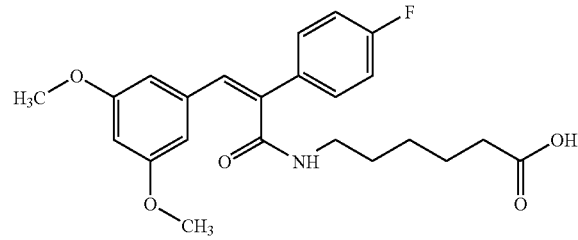

Methyl 6-{[(2Z)-3-(3,5-dimethoxyphenyl)-2-(4-fluorophenyl)prop-2-enoyl]amino}hexonate (1 g) was hydrolyzed with 1M NaOH (5 ml) in a mixture of water (2 ml) and methanol (15 ml), and the mixture was stirred at room temperature overnight. After evaporation of MeOH, the residual aqueous solution was adjusted at PH-3 with 1N HCL. The resulting precipitate was filtered and washed with water to give the pure compound (750 mg, 77.55%).

Stage 4

Synthesis of (2Z)-3-(3,5-Dimethoxyphenyl)-2-(4-fluorophenyl)-N-[6-(hydroxyamino)-6-oxohexyl]acrylamide

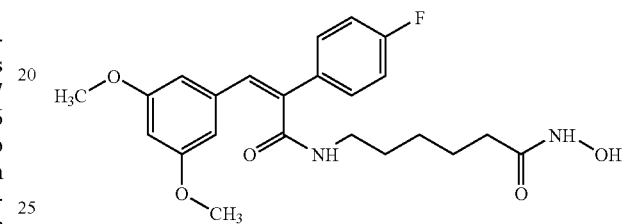

To a suspension of 6-{[(2Z)-3-(3,5-dimethoxyphenyl)-2-(4-fluorophenyl) prop-2-enoyl]amino}hexonic acid (500 mg, 1.20 mmol) in THF was added hydroxylamine hydrochloride (125 mg, 1.80 mmol), BOP reagent (637.2 mg, 1.40 mmol), and HOBT (162 mg, 1.40 mmol). DIPEA (0.55 ml, 3.60 mmol) was added dropwise with constant stirring to the above, and the reaction mixture was stirred at room temperature overnight. Subsequently the reaction mixture was evaporated to dryness, the residue was dissolved in ethyl acetate and washed successively with 1N HCL (3×50 ml), saturated NaHCO$_3$ (3×50 ml) and brine solution (3×50 ml). The organic layer was dried over Na$_2$SO$_4$ and concentrated to give the pure (2Z)-3-(3,5-dimethoxyphenyl)-2-(4-fluorophenyl)-N-[6-(hydroxyamino)-6-oxohexyl]acrylamide (450 mg, 86.87%) as an off white solid with m.p.: 104.5° C.-105° C. $^1$H NMR (DMSO-d$_6$) δ: 1.22 (3H, m), 1.46 (4H, m), 1.95 (2H, t), 3.33 (2H, q), 3.53 (6H, s), 6.15 (2H, s), 6.33 (1H, s), 7.23 (4H, m), 7.27 (1H, s), 7.48 (1H, t), 8.66 (1H, s), 10.334 (1H, s); m/z: (M+H)$^+$ at 431.1

The following compounds were prepared according to the above procedure.

| Exp. | Structure | Analytical Data |
|---|---|---|
| 2 | (structure shown) | $^1$HNMR (DMSO-d$_6$) δ: 1.26 (3H, m), 1.46 (2H, m), 2.26 (2H, t), 3.13 (2H, q), 3.35 (1H, m) 3.53 (6H, s), 6.14 (2H, s), 6.33 (1H, s), 6.42 (1H, q), 6.95 (1H, q), 7.03 (1H, q), 7.22 (5H, m) 7.32 (1H, s), 7.48 (1H, t), 9.32 (1H, s), 9.72 (1H, s); m/z: (M + H)$^+$ at 507.2; sticky compound |

| Exp. | Structure | Analytical Data |
|---|---|---|
| 3 | (3,5-dimethoxyphenyl)-CH=C(4-fluorophenyl)-C(=O)-NH-(CH2)4-C(=O)-NH-(3-hydroxyphenyl) | ¹HNMR (DMSO-d₆) δ: 1.46 (2H, m), 1.59 (2H, m), 2.26 (2H, t), 3.13 (2H, q), 3.35 (2H, m), 3.53 (6H, s), 6.14 (2H, s), 6.33 (1H, s), 6.42 (1H, q), 6.90 (1H, q), 7.03 (1H, t), 7.22 (5H, m), 7.32 (1H, s), 7.48 (1H, t), 9.32 (1H, s), 9.72 (1H, s); m/z: (M + H)⁺ at 507.2; m.p.: 147.2-147.7° C. |
| 4 | (3,5-dimethoxyphenyl)-CH=C(4-hydroxyphenyl)-C(=O)-NH-(CH2)4-C(=O)-NH-(2-aminophenyl) | ¹HNMR (DMSO-d₆) δ: 1.26 (2H, m), 1.44 (2H, m), 1.57 (2H, m), 2.39 (2H, t), 3.13 (2H, t), 3.35 (4H, m), 3.53 (6H, s), 6.19 (2H, s), 6.32 (1H, s), 6.78 (1H, m), 6.83 (2H, s), 6.97 (1H, d), 7.25 (2H, m), 7.67 (1H, d) 9.24 (1H, s), 9.57 (1H, s), 9.72 (1H, s); m/z: (M + H)⁺ at 504.2; m.p: 101.5° C.-102° C. |
| 5 | (3,5-dimethoxyphenyl)-CH=C(4-hydroxyphenyl)-C(=O)-NH-(CH2)4-C(=O)-NH-(2-hydroxyphenyl) | ¹HNMR (DMSO-d₆) δ: 1.26 (2H, m), 1.44 (2H, m), 1.57 (2H, m), 2.39 (2H, t) 3.13 (2H, t), 3.35 (2H, m), 3.53 (6H, s), 6.19 (2H, s), 6.32 (1H, s), 6.78 (1H, m), 6.83 (2H, m) 6.97 (1H, d), 7.25 (2H, m), 7.67 (1H, d) 9.24 (1H, s), 9.57 (2H, s), 9.72 (1H, s); m/z: (M + H)⁺ at 505.2; m.p. 165.2-165.7° C. |
| 6 | (3,4,5-trimethoxyphenyl)-CH=C(4-hydroxyphenyl)-C(=O)-NH-(CH2)4-C(=O)-NH-(2-hydroxyphenyl) | ¹HNMR (DMSO-d₆) δ: 1.26 (2H, m), 1.42 (2H, m), 1.59 (2H, m), 2.3 (2H, m), 3.13 (2H, m) 3.35 (2H, m), 3.49 (6H, s), 3.60 (3H, s), 6.34 (2H, s), 6.74 (1H, t), 6.83 (3H, d), 6.99 (1H, d), 7.10 (1H, t), 7.33 (1H, d), 7.67 (1H, d), 9.24 (1H, s), 9.58 (1H, s), 9.72 (1H, s); m/z: (M + H)⁺ at 535.2; m.p.: 182.5° C.-183° C. |
| 7 | (3,4,5-trimethoxyphenyl)-CH=C(4-hydroxyphenyl)-C(=O)-NH-(CH2)4-C(=O)-N(CH3)(OCH3) | ¹HNMR (DMSO-d₆) δ: 1.24 (2H, m), 1.41 (2H, m), 1.50 (2H, m), 2.34 (2H, m) 3.08 (5H, m), 3.49 (6H, s), 3.59 (3H, s) 3.64 (2H, s), 6.34 (2H, s), 6.83 (2H, d), 6.99 (2H, d), 7.11 (1H, t), 7.32 (1H, s), 9.59 (1H, s); m/z: (M + H)⁺ at 487.2; m.p.: 130.2° C.-130.7° C. |
| 8 | (4-methylthiazol-5-yl)-CH=C(thiophen-2-yl)-C(=O)-NH-(CH2)4-C(=O)-NHOH | ¹HNMR (DMSO-d₆) δ: 1.76 (4H, m), 1.46 (4H, m), 1.94 (2H, t), 3.15 (2H, q), 7.01 (1H, d), 7.21 (1H, t), 7.48 (1H, t), 7.81 (2H, s), 8.66 (1H, s), 8.89 (1H, s), 10.33 (1H, s); m/z: (M + H)⁺ at 380.0; m.p.: 98.7° C.-99.2° C. |

| Exp. | Structure | Analytical Data |
|---|---|---|
| 9 | 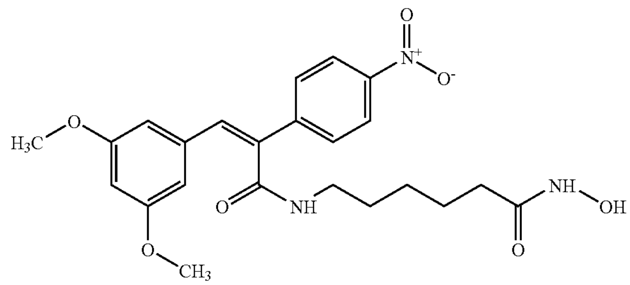 | ¹HNMR (DMSO-d₆) δ: 1.24 (2H, m), 1.46 (4H, m), 1.98 (2H, m), 3.14 (2H, q), 3.52 (6H, s), 4.16 (2H, d), 6.37 (1H, d), 7.41 (1H, s), 7.45 (1H, t), 7.79 (2H, t), 8.28 (2H, d), 8.89 (1H, s), 10.33 (1H, s); m/z: (M + H)⁺ at 458.1 |
| 10 | 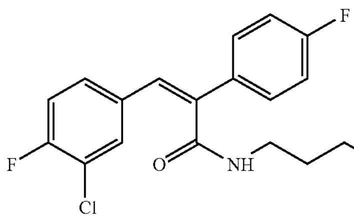 | ¹HNMR (DMSO-d₆) δ: 1.23 (2H, m), 1.46 (4H, m), 1.93 (2H, m), 3.13 (2H, q), 6.99 (1H, d), 7.15 (3H, m), 7.28 (3H, m) 7.34 (1H, s), 7.56 (1H, t), 8.99 (1H, s), 10.33 (1H, s); m/z: (M + H)⁺ at 423.1; m.p.: 163.8° C.-164.3° C. |
| 11 | 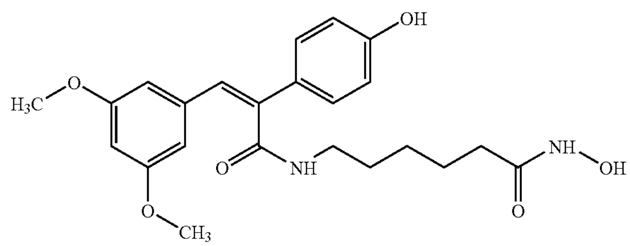 | ¹HNMR (DMSO-d₆) δ: 1.19 (2H, m), 1.40 (2H, m), 1.49 (2H, m), 1.92 (2H, t), 3.09 (2H, q) 3.53 (6H, s), 6.19 (2H, d), 6.32 (1H, t), 6.79 (1H, d), 6.95 (2H, d), 7.22 (2H, q), 8.67 (1H, s) 9.59 (1H, s), 10.33 (1H, s); m/z: (M + H)⁺ at 429.1; m.p.: 144.1° C.-144.6° C. |
| 12 | 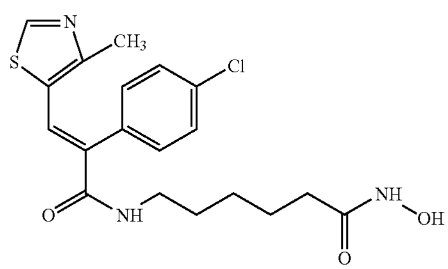 | ¹HNMR (DMSO-d₆) δ: 1.15 (3H, m), 1.18 (2H, m), 1.42 (2H, m), 1.98 (2H, q), 3.08 (2H, q), 3.35 (2H, m), 7.19 (2H, d), 7.38 (1H, t), 7.56 (2H, d), 7.72 (1H, s), 8.66 (1H, s), 8.80 (1H, s), 10.32 (1H, s); m/z: (M + H)⁺ at 408.0; m.p.: 78.5° C.-79° C. |
| 13 | 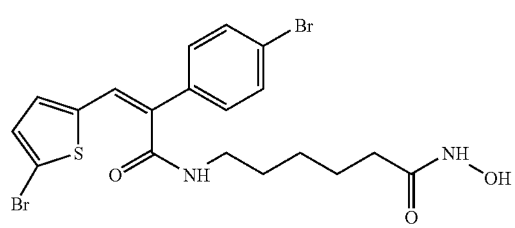 | ¹HNMR (DMSO-d₆) δ: 1.15 (3H, m), 1.19 (2H, m), 1.45 (2H, m), 1.91 (2H, q), 3.09 (2H, q), 7.18 (5H, m), 7.69 (3H, m), 8.66 (1H, s), 10.32 (1H, s); m/z: (M + H) at 516.9 |
| 14 | 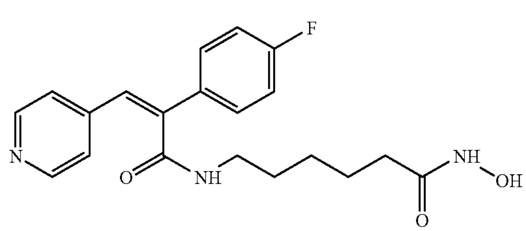 | ¹HNMR (DMSO-d₆) δ: 1.18 (4H, m), 1.57 (2H, m), 1.99 (2H, S), 2.50 (2H, s), 7.42 (3H, m), 7.36 (1H, s), 7.56 (3H, m), 7.98 (3H, d), 10.37 (1H, s), 1.50 (1H, s), 13.64 (1H, d); m/z: (M + H)⁺ at 372.1, m.p. 101.2° C.-105.5° C. |

-continued

| Exp. | Structure | Analytical Data |
|---|---|---|
| 15 | 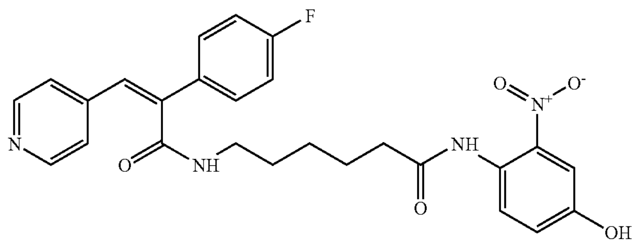 | ¹HNMR (DMSO-d₆) δ: 1.25 (2H, m), 1.34 (2H, m), 1.49 (2H, m), 1.92 (2H, s), 3.17 (2H, s), 3.37 (2H, m), 5.16 (1H, s), 6.75 (2H, d), 6.91 (2H, d), 7.16 (1H, s), 7.19 (4H, m), 7.71 (1H, d), 8.36 (2H, s); m/z: (M + H)⁺ at 493.1. |
| 16 | 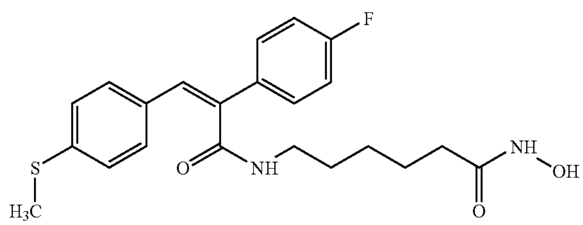 | ¹H NMR (DMSO-d₆) δ: 1.20 (2H, s), 1.46 (4H, m), 1.94 (2H, t), 2.41 (3H, s), 3.08 (2H, t), 6.89 (2H, d), 7.06 (2H, d), 7.20 (4H, m), 7.34 (1H, s), 8.66 (1H, s), 10.33 (1H, s); m/z: (M + H)⁺ at 417.1; m.p.: 168.1° C.-170.9° C. |
| 17 | 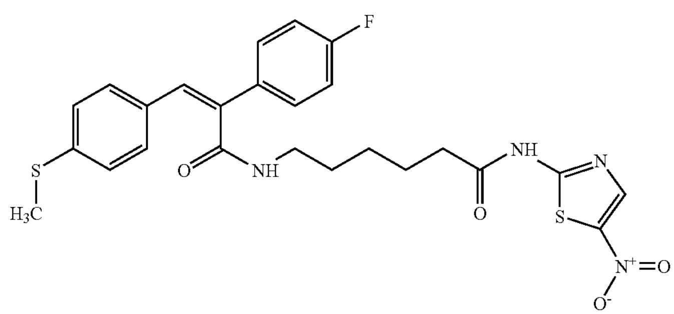 | ¹HNMR (DMSO-d₆) δ: 1.28 (2H, m), 1.45 (2H, m), 1.62 (2H, m), 2.41 (3H, s), 2.50 (2H, t), 3.12 (2H, t), 6.89 (2H, d), 7.06 (2H, d), 7.18 (4H, m), 7.32 (1H, s), 8.61 (1H, s), 13.05 (1H, s); m/z: (M + H)⁺ at 529.1; m.p.201.4° C.-205.9° C. |
| 18 | 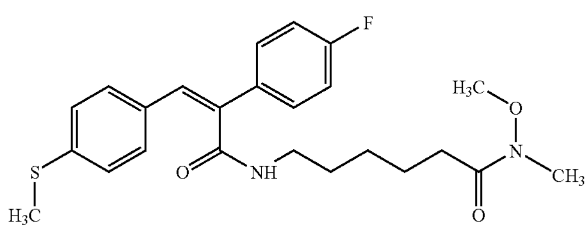 | ¹HNMR (DMSO-d₆) δ: 1.27 (4H, m), 1.47 (4H, m), 2.41 (3H, s), 3.07 (5H, m), 3.64 (3H, s), 6.91 (2H, d), 7.06 (2H, d), 7.20 (4H, m), 7.34 (1H, s); m/z: (M + H)⁺ at 445.1, m.p.: 205.4° C.-209.1° C. |
| 19 | 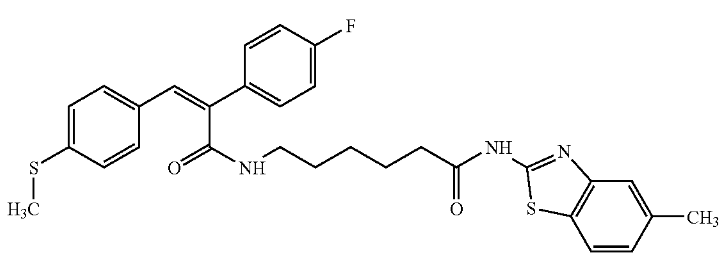 | ¹HNMR (DMSO-d₆) δ: 1.20 (2H, m), 1.45 (4H, m), 1.94 (2H, t), 2.41 (3H, s), 3.08 (2H, t), 6.87 (1H, d), 7.02 (1H, d), 7.05 (3H, d), 7.20 (2H, d), 7.31 (2H, s), 7.59 (2H, d), 7.73 (1H, s); m/z: (M + H)⁺ at 548.1 |
| 20 | 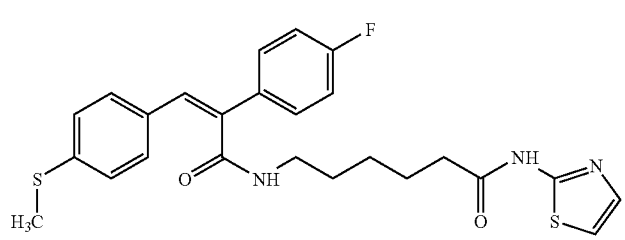 | ¹HNMR (DMSO-d₆) δ: 1.26 (2H, m), 1.44 (2H, m), 1.59 (2H, m), 2.42 (3H, s), 2.50 (2H, s), 3.11 (2H, s), 3.36 (4H, m), 6.89 (4H, d), 7.33 (1H, s), 7.44 (2H, d), 12.05 (1H, s); m/z: (M + H)⁺ at 484.1; m.p.: 158.1-159.6° C. |

| Exp. | Structure | Analytical Data |
|---|---|---|
| 21 | 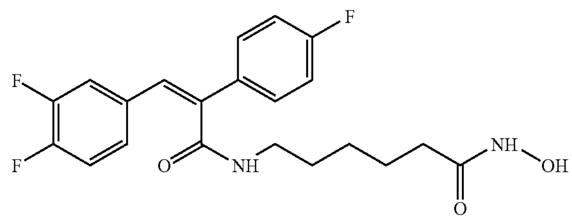 | $^1$H NMR (DMSO-d$_6$) δ: 1.20 (2H, q), 1.45 (4H, m), 1.92 (2H, t), 3.12 (2H, q), 6.85 (1H, s), 6.94 (1H, d), 7.20 (5H, t), 7.24 (1H, s), 7.55 (1H, t), 8.65 (1H, d), 10.34 (1H, s); m/z: (M + H)$^+$ at 407; m.p.: 135.8° C.-139.4° C. |
| 22 | 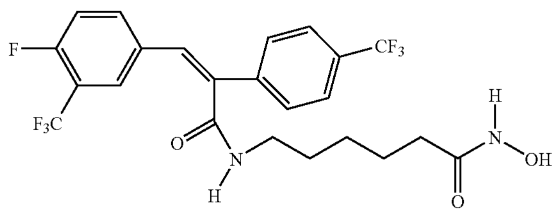 | $^1$H NMR (DMSO-d$_6$) δ: 1.19-1.23 (2H, q), 1.42-1.46 (4H, m), 1.91-1.94 (2H, t), 2.50 (2H, q), 7.13 (1H, s), 7.22-7.35 (4H, m), 7.50 (1H, s), 7.77-7.79 (3H, m), 8.69 (1H, t), 8.65 (1H, s), 10.35 (1H, s); m/z: (M + H)$^+$ at 507.1; m.p.: 95.1-103.6° C. |
| 23 | 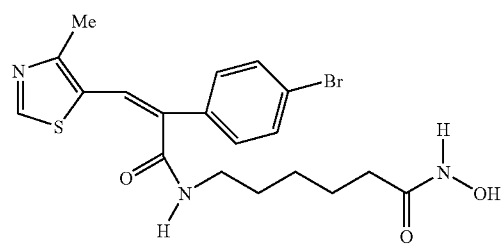 | $^1$H NMR (DMSO-d$_6$) δ: 1.17-1.19 (2H, q), 1.38-1.48 (4H, m), 1.90-1.93 (2H, t), 3.08-3.10 (2H, q), 6.85 (1H, s), 7.12-7.14 (2H, dd), 7.38-7.40 (1H, s), 7.68-7.70 (2H, dd), 7.72 (1H, d), 8.66 (1H, t), 8.80 (1H, s), 10.33 (1H, s); m/z: (M + 2)$^+$ at 454.1; hygroscopic |
| 24 | 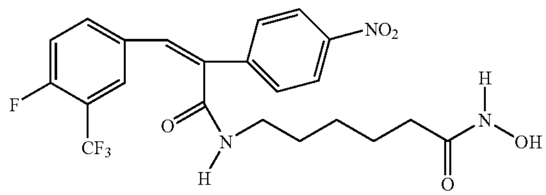 | $^1$H NMR (DMSO-d$_6$) δ: 1.24-1.26 (2H, q), 1.44-1.51 (4H, m), 1.92-1.96 (2H, t), 3.13-3.16 (2H, q), 6.66 (1H, s), 6.98 (1H, d), 7.04-7.05 (1H, d), 7.13 (2H, dd), 7.50 (2H, dd), 7.62-7.63 (1H, d), 8.10-8.12 (1H, t), 8.67 (1H, s), 10.34 (1H, s); m/z: (M + H)$^+$ at 483.9; m.p.: 128.8-134.9° C. |
| 25 | 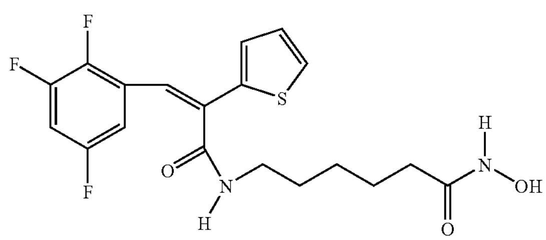 | $^1$H NMR (DMSO-d$_6$) δ: 1.21-1.22 (2H, q), 1.40-1.48 (2H, m), 1.91-1.95 (2H, t), 3.10-3.11 (2H, q), 6.99 (1H, m), 7.14-7.56 (7H, m), 7.56 (1H, t), 8.16 (1H, t), 8.90 (1H, s), 10.34 (1H, s); m/z: (M + H)$^+$ at 412.9; hygroscopic |
| 26 | 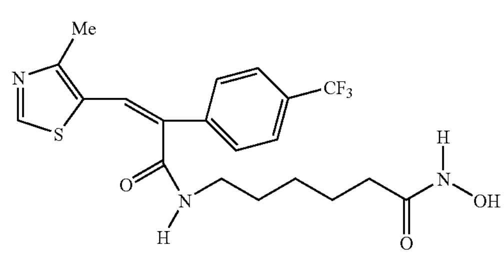 | $^1$H NMR (DMSO-d$_6$) δ: 1.02 (3H, s), 1.17-1.21 (2H, q), 1.39-1.49 (4H, m), 1.90-1.94 (2H, t), 3.10-3.11 (2H, q), 7.41-7.43 (2H, dd), 7.53-7.56 (1H, d), 7.52 (1H, s), 7.84 (2H, dd), 8.67 (1H, s), 8.81 (1H, s), 10.34 (1H, s); m/z: (M + H)$^+$ at 441.8; m.p.: 66.1-75.2° C. |

| Exp. | Structure | Analytical Data |
|---|---|---|
| 27 | 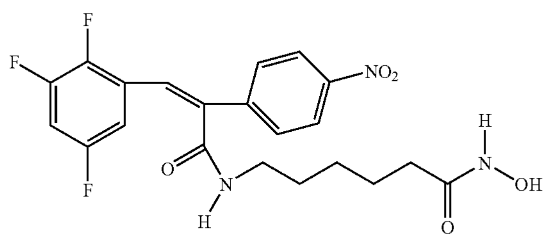 | $^1$H NMR (DMSO-d$_6$) δ: 1.19-1.23 (2H, q), 1.42-1.46 (4H, m), 1.91-1.94 (2H, t), 2.50 (2H, q), 6.57 (1H, s), 7.30-7.47 (4H, m), 8.00 (1H, t), 8.20-8.22 (2H, m), 8.64 (1H, t), 8.68 (1H, s), 10.35 (1H, s); m/z: (M + H)$^+$ at 452.8; hygroscopic |
| 28 | 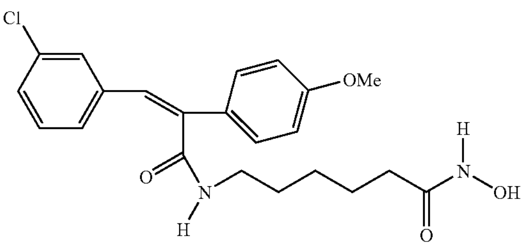 | $^1$H NMR (DMSO-d$_6$) δ: 1.19-1.22 (2H, q), 1.41-1.45 (4H, m), 1.91-1.94 (2H, t), 2.52 (2H, q), 3.78 (3H, s), 7.13 (1H, s), 6.97-6.99 (4H, m), 7.06-7.08 (2H, dd), 7.24-7.25 (2H, dd), 7.27 (1H, s), 7.47 (1H, s), 8.65 (1H, s), 10.35 (1H, s); m/z: (M + H)$^+$ at 417.1; hygroscopic |
| 29 | 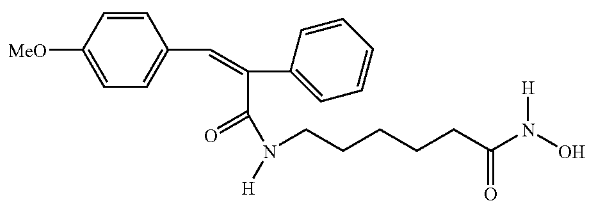 | $^1$H NMR (DMSO-d$_6$) δ: 1.20-1.22 (2H, q), 1.39-1.43 (4H, m), 1.90-1.92 (2H, t), 2.50 (2H, q), 3.68 (3H, s), 6.71-6.73 (2H, dd), 6.89-6.91 (2H, dd), 7.15-7.44 (7H, m), 8.67 (1H, s), 10.33 (1H, s); m/z: (M + H)$^+$ at 383.2; m.p.: 117.2-119.6° C. |
| 30 | 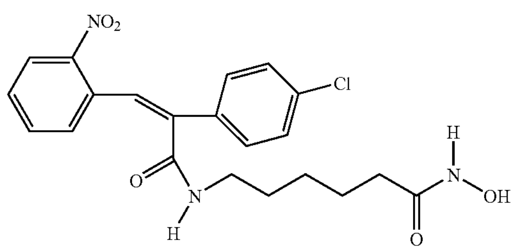 | $^1$H NMR (DMSO-d$_6$) δ: 1.16-1.29 (4H, m), 1.44-1.53 (4H, m), 1.95-2.21 (2H, t), 6.96-6.97 (1H, dd), 6.98-7.03 (2H, dd), 7.31-7.33 (2H, dd), 7.48-7.7.49 (2H, t), 7.58 (1H, s), 7.79-7.80 (1H, m), 8.07-8.09 (1H, m), 8.69 (1H, s), 10.36 (1H, s); m/z: (M + H)$^+$ at 432.1; sticky material |
| 31 | 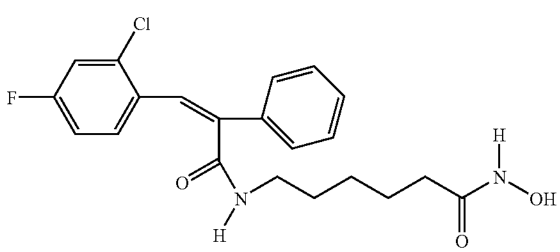 | $^1$H NMR (DMSO-d$_6$) δ: 1.34-1.35 (2H, m), 1.53-1.56 (4H, m), 1.61-1.65 (2H, t), 2.07-2.11 (2H, t), 3.35 (2H, m), 6.71-6.76 (2H, m), 7.13-7.15 (2H, dd), 7.22-7.24 (1H, dd), 7.34-7.35 (2H, m), 7.57 (1H, s), 7.59 (1H, s), 8.69 (1H, s), 10.36 (1H, s); m/z: (M + H)$^+$ at 405.1; m.p.: 156.2-166.9° C. |
| 32 | 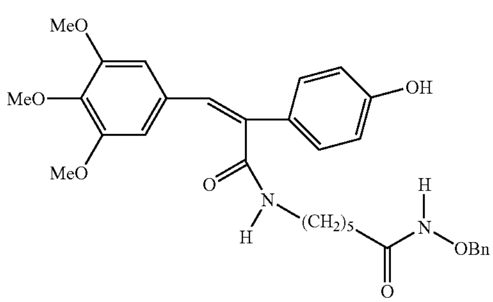 | $^1$H NMR (DMSO-d$_6$) δ: 1.18-1.19 (2H, m), 1.37-1.47 (4H, m), 1.91-1.93 (2H, t), 3.09-3.10 (2H, t), 3.48 (6H, s), 3.59 (3H, s), 4.77 (2H, s), 6.33 (1H, s), 6.83-6.85 (2H, dd), 6.97-6.99 (2H, dd), 7.10 (1H, t), 7.32-7.36 (6H, m), 9.60 (1H, s), 10.94 (1H, s); m/z: (M + H)$^+$ at 549.2; hygroscopic |

| Exp. | Structure | Analytical Data |
|---|---|---|
| 33 | (3,5-dimethoxyphenyl)-CH=C(4-F-C6H4)-C(O)NH-(CH2)5-C(O)NH-OBn | ¹H NMR (DMSO-d₆) δ: 1.08-1.26 (2H, m), 1.39-1.48 (4H, m), 1.94-1.98 (2H, t), 3.09-3.11 (2H, t), 3.52 (6H, s), 4.77 (2H, s), 4.79 (1H, s), 6.14-6.15 (2H, d), 6.33 (1H, t), 7.19-7.22 (4H, m), 7.24 (1H, dd), 7.34-7.36 (4H, m), 7.48 (1H, s), 10.94 (1H, s); m/z: (M + H)⁺ at 521.2; m.p.: 79.9-86.7° C. |
| 34 | (3,4-difluorophenyl)-CH=C(4-F-C6H4)-C(O)NH-(CH2)5-C(O)NHOH | ¹H NMR (DMSO-d6) δ: 1.19-1.24 (2H, m), 1.40-1.51 (4H, m), 1.91-1.95 (2H, m), 3.08-3.13 (2H, m), 6.85 (1H, s), 6.86-6.96 (1H, m), 7.17-7.34 (6H, m) 8.63-6.67 (2H, s), 10.34 (1H, s); m/z: (M + H)⁺ at 407.1; m.p: 135.8-139.4° C. |
| 36 | (3,4-difluorophenyl)-CH=C(4-F-C6H4)-C(O)NH-(CH2)5-C(O)NH-thiazol-2-yl | ¹H NMR (DMSO-d6) δ: 1.24-1.27 (3H, m), 1.43-1.45 (3H, m), 1.57-1.61 (2H, m), 2.40-2.43 (2H, m), 7.20-7.44 (8H, m), 7.45-7.53 (1H, m), 7.55-7.56 (1H, m), 12.05 (2H, s); m/z: (M + H)⁺ at 474.2; m.p.: 199.1-202.3° C. |
| 37 | (5-chlorofuran-2-yl)-CH=C(4-F-C6H4)-C(O)NH-(CH2)5-C(O)NHOH | ¹H NMR (DMSO-d6) δ: 1.18-1.19 (2H, m), 1.37-1.48 (4H, m), 1.90-1.93 (2H, m), 3.07-3.09 (2H, m), 5.96-5.97 (1H, m), 6.43-6.44 (1H, m), 7.32-7.34 (5H, m), 8.68 (2H, s), 10.34 (1H, s); m/z: (M + H)⁺ at 395.1; m.p.: 121.1-127.2° C. |
| 38 | (4-MeS-C6H4)-CH=C(4-CF3-C6H4)-C(O)NH-(CH2)5-C(O)NHOH | ¹H NMR (DMSO-d6) δ: 1.22-1.25 (2H, m), 1.43-1.52 (4H, m), 1.91-1.95 (2H, m), 2.41 (3H, s), 3.08-3.11 (2H, m), 6.89-6.91 (2H, m), 7.06-7.08 (2H, m), 7.37-7.38 (3H, m), 7.65-7.66 (2H, m), 7.75-7.77 (1H, m), 8.67 (1H, s), 10.34 (1H, s); m/z: (M + H)⁺ at 467.2; m.p.: 132.5-133.8° C. |
| 39 | (thiazol-2-yl)-CH=C(4-CF3-C6H4)-C(O)NH-(CH2)5-C(O)NHOH | ¹H NMR (DMSO-d6) δ: 1.03-1.04 (2H, m), 1.19-1.22 (2H, m), 1.41-1.50 (4H, m), 3.12-3.59 (2H, m), 7.49-7.51 (2H, m), 7.66-7.67 (1H, m), 7.72 (1H, s), 7.77-7.80 (1H, s), 7.86-7.90 (2H, m), 8.66-8.67 (2H, m), 10.33 (1H, s); m/z: (M + H)⁺ at 428.0; off white sticky solid; |

| Exp. | Structure | Analytical Data |
|---|---|---|
| 40 | 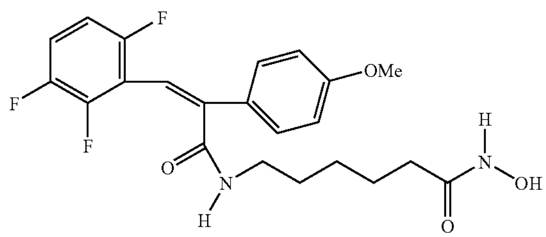 | $^1$H NMR (DMSO-d6) δ: 1.22-1.25 (2H, m), 1.44-1.50 (4H, m), 1.92-1.96 (2H, m), 3.13-3.16 (2H, m), 3.31 (4H, m), 6.90 (1H, s), 6.96-6.98 (2H, m), 7.05 (1H, s), 7.16-7.18 (1H, m), 7.40-7.41 (1H, m), 7.85 (1H, m), 10.35 (1H, s); m/z: (M + H)$^+$ at 437.1; pale brown sticky solid |
| 41 | 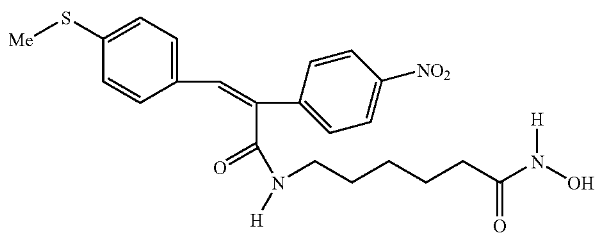 | $^1$H NMR (DMSO-d6) δ: 1.22-1.27 (2H, m), 1.43-1.48 (4H, m), 1.91-1.95 (1H, m), 2.20 (1H, s), 2.41 (3H, s), 3.10-3.12 (2H, m), 6.91-6.93 (2H, m), 7.06-7.09 (2H, m), 7.45-7.51 (3H, m), 7.70-7.74 (1H, m), 8.25-8.27 (1H, m), 8.67 (1H, s), 10.34 (1H, s), 12.0 (1H, s); m/z: (M + H)$^+$ at 444.1; m.p. 138.2-143.9° C. |
| 42 | 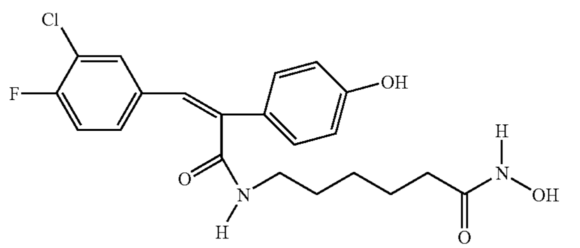 | $^1$H NMR (DMSO-d6) δ: 1.18-1.23 (2H, m), 1.38-1.49 (4H, m), 1.91-1.94 (2H, m), 3.07-3.12 (2H, m), 6.80-6.82 (2H, m), 6.94-6.96 (2H, m), 7.03-7.04 (1H, m), 7.15-7.16 (1H, m), 7.24-7.28 (2H, m), 7.32-7.34 (1H, m), 8.67 (1H, s), 9.88 (1H, s), 10.35 (1H, s); m/z: (M + H)$^+$ at 421.1; m.p. 100.3-103.9° C. |
| 43 | 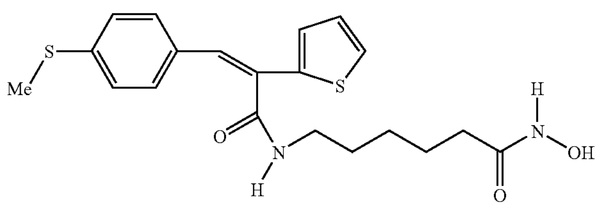 | $^1$H NMR (DMSO-d6) δ: 1.20-1.23 (2H, m), 1.41-1.50 (4H, m), 1.91-1.95 (2H, m), 2.44 (3H, s), 3.11-3.15 (2H, m), 6.96 (1H, s), 7.02-7.04 (2H, m), 7.10-7.12 (3H, m), 7.38 (1H, s), 7.59-7.65 (2H, m), 8.78 (1H, s), 10.23 (1H, s); m/z: (M + H)$^+$ at 405.1; m.p. 147.1-149.9° C. |
| 44 | 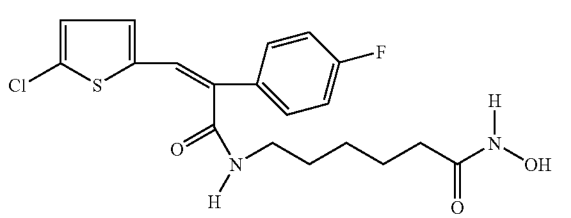 | $^1$H NMR (DMSO-d6) δ: 1.15-1.18 (2H, m), 1.36-1.47 (4H, m), 1.89-1.93 (2H, m), 3.06-3.08 (2H, m), 7.03 (1H, s), 7.17-7.20 (1H, m), 7.23-7.26 (3H, m), 7.34-7.38 (2H, m), 7.68 (1H, s), 8.68 (1H, s), 10.33 (1H, s); m/z: (M + H)$^+$ at 411.1; m.p. 181-185.2° C. |
| 45 | 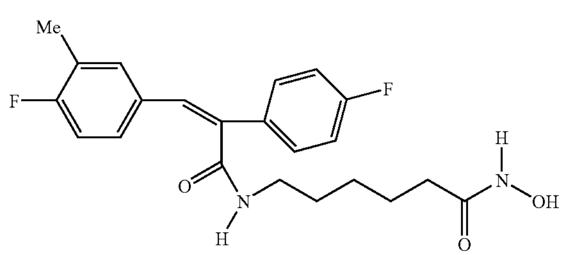 | $^1$H NMR (DMSO-d6) δ: 1.18-1.24 (2H, m), 1.40-1.48 (4H, m), 1.91-1.95 (2H, m), 2.07 (3H, m), 3.08-3.11 (2H, m), 6.74-6.77 (1H, m), 6.93-6.98 (2H, m), 7.16-7.19 (2H, m), 7.22-7.27 (2H, m), 7.34 (1H, s), 7.48 (1H, s), 8.68 (1H, s), 10.34 (1H, s); m/z: (M + H)$^+$ at 411.1; m.p.: 161.2-163.1° C. |

-continued

| Exp. | Structure | Analytical Data |
|---|---|---|
| 46 | (structure: 3-MeO-4-HO-phenyl / 4-F-phenyl acrylamide linked to -NH-(CH2)5-C(O)-NHOH) | ¹H NMR (DMSO-d6) δ: 1.18-1.23 (2H, m), 1.38-1.49 (4H, m), 1.90-1.94 (2H, m), 3.08-3.11 (2H, m), 3.32 (3H, s), 6.37 (1H, s), 6.55-6.57 (1H, m), 6.61-6.63 (1H, m), 7.19-7.21 (2H, m), 7.22-7.30 (3H, m), 7.34 (1H, s), 8.67 (1H, s), 9.34 (1H, s), 10.34 (1H, s); m/z: (M + H)⁺ at 417.1; m.p.: 162-167° C. |
| 47 | (structure: 4-CF3-phenyl / 4-F-phenyl acrylamide linked to -NH-(CH2)5-C(O)-NHOH) | ¹H NMR (DMSO-d6) δ: 1.22-1.24 (2H, m), 1.42-1.50 (4H, m), 1.92-1.95 (2H, m), 3.11-3.12 (2H, m), 7.03-7.09 (4H, m), 7.36-7.38 (2H, m), 7.42 (1H, s), 7.72-7.76 (3H, m), 8.68 (1H, s), 10.35 (1H, s); m/z: (M + H)⁺ at 439.1; m.p.: 103-105.2° C. |
| 48 | (structure: 3,4,5-triMeO-phenyl / 4-F-phenyl acrylamide linked to -NH-(CH2)5-C(O)-NHOH) | ¹H NMR (DMSO-d6) δ: 1.20-1.21 (2H, m), 1.39-1.43 (4H, m), 1.91-1.94 (2H, m), 3.09-3.11 (2H, m), 3.34 (6H, s), 3.60 (3H, s), 6.30 (2H, s), 7.21-7.24 (4H, m), 7.29-7.31 (1H, m), 7.38 (1H, s), 8.76 (1H, s), 10.34 (1H, s); m/z: (M + H)⁺ at 461.1; m.p: 153-157° C. |
| 49 | (structure: 3,5-diMeO-phenyl / 4-NO2-phenyl acrylamide linked to -NH-(CH2)5-C(O)-NH-(CH2)3-C(O)-NHOH) | ¹H NMR (DMSO-d₆) δ: 1.67-1.69 (2H, t), 1.93-2.07 (8H, m), 2.79-2.82 (2H, t), 3.15-3.19 (4H, m), 3.52 (6H, s), 7.47-7.49 (3H, m), 7.55 (1H, s), 7.98-8.00 (2H, dd), 8.25-8.27 (2H, dd), 8.69 (1H, s), 10.36 (1H, s), 12.05 (1H, s), 13.63 (1H, s); m/z: (M + H)⁺ at 501.5; hygroscopic |
| 50 | (structure: 3,4,5-triMeO-phenyl / 4-OMe-phenyl acrylamide linked to -NH-(CH2)6-C(O)-NHOH) | ¹H NMR (DMSO-d6) δ: 1.19-1.20 (2H, m), 1.38-1.58 (4H, m), 1.90-1.94 (2H, m), 3.09-3.10 (2H, m), 3.47 (6H, s), 3.59 (3H, s), 3.77 (3H, s), 6.32 (2H, s), 7.02-7.04 (2H, m), 7.10-7.12 (2H, m), 7.19 (1H, s), 7.34 (2H, s), 8.56 (1H, s); m/z: (M + H)⁺ at 473.2; Red sticky liquid; |
| 51 | (structure: 4-MeS-phenyl / 4-F-phenyl acrylamide linked to -NH-(CH2)6-C(O)-NH-O-bn) | ¹H NMR (DMSO-d6) δ: 1.20-1.25 (2H, m), 1.39-1.48 (4H, m), 1.92-1.94 (2H, m), 2.41 (3H, s), 3.09-3.11 (2H, s), 4.77 (2H, s), 6.88-6.91 (2H, m), 7.04-7.06 (2H, m), 7.18-7.33 (4H, m), 7.35-7.37 (6H, m), 7.44 (1H, s), 10.95 (1H, s); m/z: (M + H)⁺ at 507.1; m.p.: 134-136° C. |

EXAMPLE 52

Synthesis of N-acetyl-6-{[(2Z)-3-(4-thiomethylphenyl)-2-(4-fluorophenyl)-acrylamide]}-N-hydroxy-hexanamide

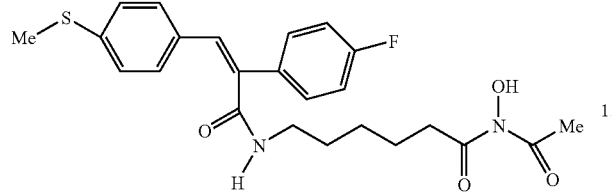

To a solution of (2Z)-3-(4-Thiomethylphenyl)-2-(4-fluorophenyl)-N-[6-(hydroxyamine)-6-oxohexyl]acrylamide (prepared following the similar procedure described for example 1) in dichloromethane (5 mL), pyridine (0.27 mL, 3.96 mmol) was added and cooled to 0° C. followed by the dropwise addition of acetyl chloride (0.25 mL, 3.6 mmol) and the reaction mixture was stirred for 1 h. The reaction mixture was diluted with dichloromethane (30 mL) and washed with water, the organic layer was dried on anhydrous $Na_2SO_4$, concentrated and triturated with dichloromethane/hexane (1:1) (20 mL) to afford 0.06 g (35% yield) of the title compound as a colorless sticky mass. $^1$H NMR (DMSO-$d_6$) δ: 1.23-1.26 (2H, m), 1.40-1.53 (4H, m), 2.08-2.13 (3H, m), 2.50 (3H, m), 2.72-2.88 (2H, m), 3.09-3.11 (2H, m), 6.89-6.91 (2H, m), 7.05-7.07 (2H, m), 7.16-7.26 (4H, m), 7.33 (1H, s), 7.44 (1H, s), 11.35 (1H, s); and m/z: (M+H)$^+$ at 437.2
The following compound was prepared according to the above procedure:

EXAMPLE 54

Synthesis of N-hydroxy-2-{[(2Z)-3-(4-thiomethylphenyl)-2-(4-fluorophenyl)-acrylamide]6-oxohexyl]amino}-3-(4-hydroxyphenyl)propanamide

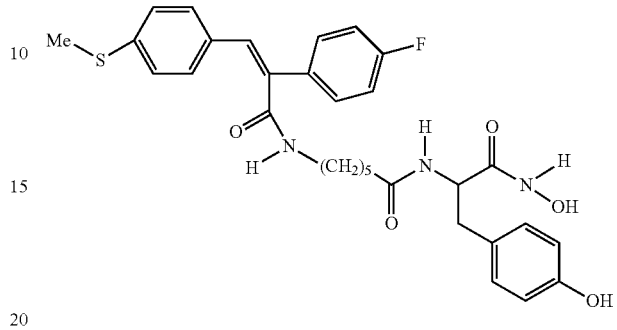

Stage 1

Synthesis of Methyl-2-{[(2Z)-3-(4-thiomethylphenyl)-2-(4-fluorophenyl)-acrylamide]6-oxohexyl]amino}-3-(4-hydroxyphenyl)propanoate

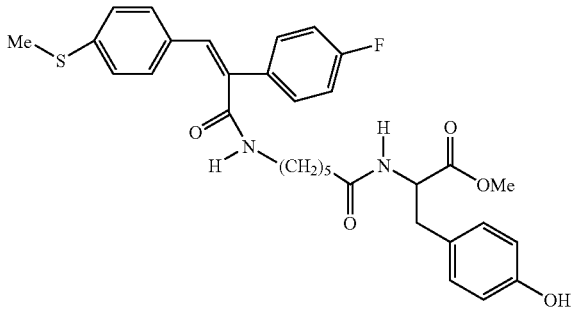

To a solution of 6-{[(2Z)-3-(4-Thiomethylphenyl)-2-(4-fluorophenyl) prop-2-enoyl]amino}hexonic acid (0.050 g, 0.12 mmol) (prepared according to the procedure described in

| Exp. | Structure | Analytical Data |
| --- | --- | --- |
| 53 | 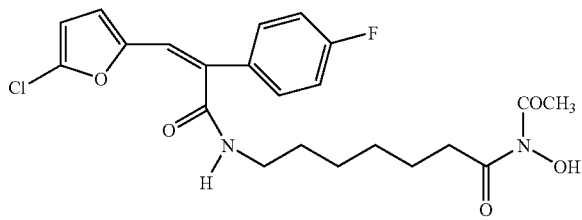 | $^1$H NMR (DMSO-d6) δ: 1.22-1.23 (3H, m), 1.38-1.42 (2H, m), 1.48-1.52 (2H, m), 2.07-2.50 (4H, m), 3.35 (2H, m), 5.96-5.97 (1H, m), 6.43-6.44 (1H, m), 7.23-7.35 (5H, m), 10.33 (1H, s), 11.55 (1H, s); m/z: (M + H)$^+$ at 437.2; pale brown sticky liquid | example 1 stage 3) in THF (3 mL) was added DIPEA (0.06 mL, 0.37 mmol), BOP (0.065 g, 0.14 mmol), HOBt (0.020 g, 0.14 mmol) followed by the methyl ester of tyrosine (0.029 g, 0.14 mmol). The reaction was stirred at room temperature for 12 hours, THF was removed under reduced pressure, the crude was taken up in EtOAc (25 mL), washed with water, and the organic layer was dried over anhydrous $Na_2SO_4$, concentrated and purified by silica gel column chromatography using dichloromethane/MeOH (9.8:0.2) to afford Methyl-2-{[(2Z)-3-(4-thiomethyl phenyl)-2-(4-fluorophenyl)-acrylamide]6-oxohexyl]amino}-3-(4-hydroxyphenyl)propanoate 0.040 g, 55% yield as an off-white solid.

Stage 2

Synthesis of N-hydroxy-2-{[(2Z)-3-(4-thiomethylphenyl)-2-(4-fluorophenyl)-acrylamide]6-oxohexyl]amino}-3-(4-hydroxyphenyl)propanamide

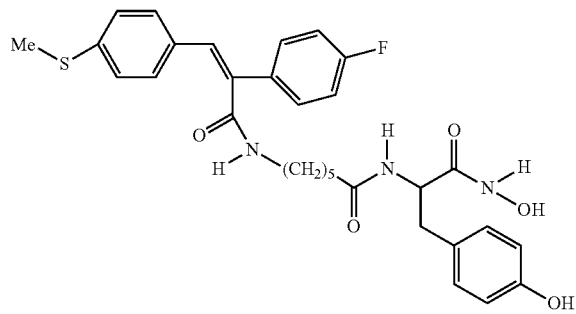

Hydroxylamine hydrochloride (0.086 g, 1.2 mmol) in methanol (2 mL) was mixed with KOH (0.069 g, 1.2 mmol) in methanol (3 mL) at 40° C., and cooled to 0° C. when a white precipitate was formed which was filtered. The filtrate was immediately added to the Methyl-2-{[(2Z)-3-(4-thiomethylphenyl)-2-(4-fluorophenyl)-acrylamide]6-oxohexyl]amino}-3-(4-hydroxyphenyl)propanoate (0.040 g, 0.06 mmol) followed by the addition of KOH (0.0057 g, 0.13 mmol), and the mixture was stirred at room temperature, for 1 hour. Around 20 mL of water was added and neutralized to a pH of 7 by dilute AcOH. On standing a colorless precipitate started was formed which was filtered, dried and triturated with dichloromethane/hexanes (1:1, 20 mL), to afford the required compound as a pure colorless solid (0.025 g, 62.5%). $^1$H NMR (DMSO-$d_6$) δ: 1.02-1.04 (2H, m), 1.10 (1H, s), 1.99-2.01 (2H, m), 2.41 (3H, s), 2.50-2.67 (2H, m), 3.06-3.08 (2H, m), 4.47 (1H, s), 6.02-6.62 (2H, m), 6.89-6.91 (2H, m), 6.97-6.99 (2H, m), 7.05-7.07 (2H, m), 7.18-7.24 (4H, m), 7.34 (4H, s), 7.42 (1H, s), 8.00 (1H, s), 8.82 (1H, s), 9.15 (1H, s), 10.61 (1H, s); and m/z: (M+H)$^+$ at 580.1; m.p.: 142.1-145.4° C.

The following compounds were prepared according to the above procedure:

| Exp. | Structure | Analytical Data |
|---|---|---|
| 55 | (structure with MeO-tetrafluorophenyl, 4-fluorophenyl acrylamide, hexyl linker, tyrosine OMe ester) | $^1$H NMR (DMSO-d6) δ: 1.17-1.19 (2H, m), 1.41-1.44 (4H, m), 2.04-2.08 (2H, m), 2.50 (2H, s), 3.11-3.13 (2H, m), 3.57 (3H, s), 4.03 (3H, s), 4.7 (1H, s), 6.63-6.65 (2H, m), 6.95-6.99 (3H, m), 7.12-7.14 (4H, m), 7.97 (1H, s), 8.19-8.20 (1H, s), 9.21 (1H, s); m/z: (M + H)$^+$ at 635.2; white hygroscopic solid |
| 56 | (structure with 4-fluorophenyl, tetrafluoro-4-methoxyphenyl acrylamide, hexyl linker, tyrosine NHOH) | $^1$H NMR (DMSO-d6) δ: 1.13-1.15 (2H, m), 1.23 (2H, s), 1.37-1.43 (4H, m), 2.01-2.05 (2H, m), 3.10-3.12 (2H, m), 4.02 (3H, s), 5.75 (1H, s), 6.61-6.63 (2H, m), 6.95-6.99 (3H, m), 7.12-7.14 (4H, m), 7.95-8.02 (2H, m), 8.80 (1H, s), 9.14 (1H, s), 10.06 (1H, s); m/z: (M + H)$^+$ at 636.1; m.p.: 162.4-165.2° C. |

| Exp. | Structure | Analytical Data |
|---|---|---|
| 57 | 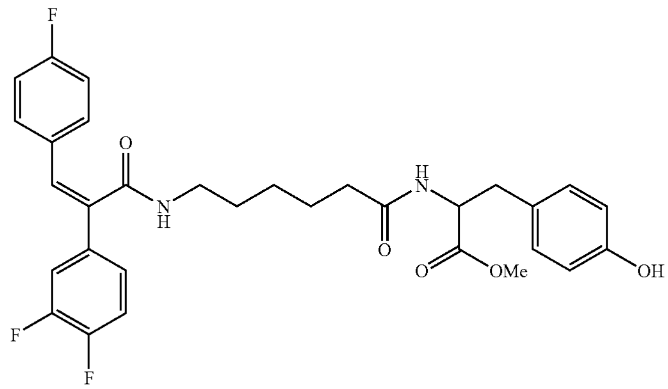 | $^1$H NMR (DMSO-d6) δ: 1.14-1.16 (2H, m), 1.24-1.25 (2H, m), 1.37-1.43 (4H, m), 2.03-2.06 (2H, m), 3.06-3.33 (2H, m), 3.57 (3H, s), 4.35 (1H, s), 6.63-6.65 (2H, m), 6.85 (1H, m), 6.92-6.98 (3H, m), 7.17-7.21 (2H, m), 7.23-7.34 (3H, m), 7.51-7.54 (1H, m), 8.17 (1H, s), 8.19 (1H, s), 9.2 (1H, s); m/z: (M + H)$^+$ at 569.1; creamy white hygroscopic solid |
| 58 | 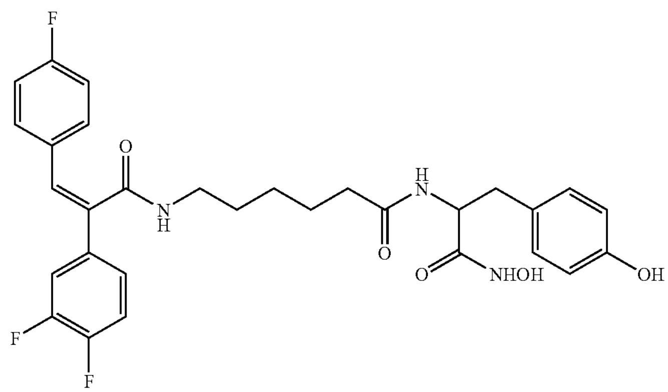 | $^1$H NMR (DMSO-d6) δ: 1.09-1.12 (2H, m), 1.23-1.29 (2H, m), 1.33-1.39 (4H, m), 2.2-2.03 (2H, m), 3.07-3.08 (2H, m), 5.39 (1H, s), 6.60-6.62 (2H, m), 6.95-6.99 (1H, m), 7.17-7.28 (3H, m), 7.30 (2H, s), 7.34 (2H, s), 7.51 (2H, s), 7.99 (1H, s), 8.02 (1H, s), 8.81 (1H, s), 9.14 (1H, s) 10.64 (1H, s); m/z: (M + H)$^+$ at 570.1; Pale yellow hygroscopic solid |
| 59 | 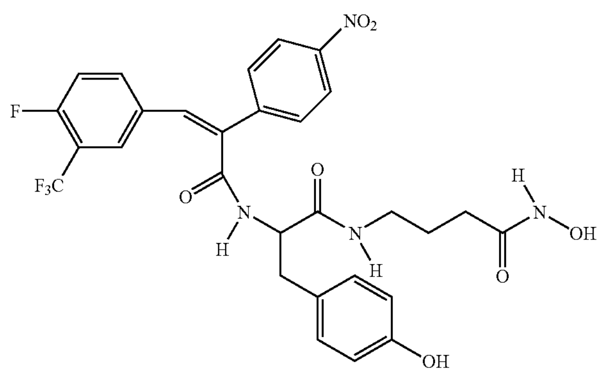 | $^1$H NMR (DMSO-d$_6$) δ: 2.66-2.69 (2H, d), 2.85-2.89 (2H, t), 3.49-3.52 (1H, t), 4.21-4.25 (2H, t), 4.31-4.33 (2H, m), 6.65-6.67 (2H, dd), 7.01-7.03 (2H, dd), 7.29-7.37 (2H, m), 7.39-7.42 (3H, m), 7.72-7.74 (2H, m), 8.20-8.22 (2H, dd), 8.51 (1H, s), 9.62 (1H, s), 10.94 (1H, s); m/z: (M + H)$^+$ at 519.2; hygroscopic |
| 60 | 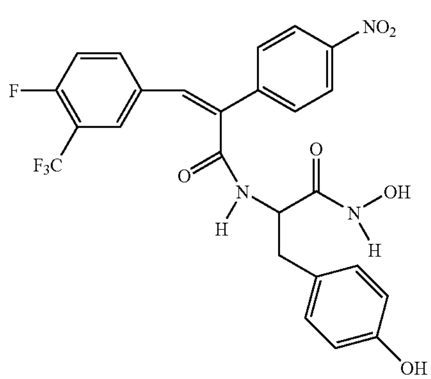 | $^1$H NMR (DMSO-d$_6$) δ: 2.78-2.86 (2H, m), 4.46 (1H, t), 6.65-6.67 (2H, dd), 7.00-7.02 (2H, dd), 7.28-7.30 (3H, m), 7.35-7.39 (3H, m), 7.99-8.02 (1H, d), 8.20-8.22 (2H, d), 8.91 (2H, s), 9.22 (1H, s), 10.72 (1H, s); m/z: (M + H)$^+$ at 534.0; off white solid hygroscopic |

-continued

| Exp. | Structure | Analytical Data |
|---|---|---|
| 61 | 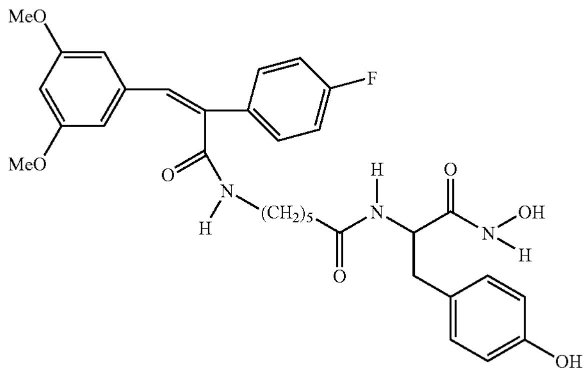 | $^1$H NMR (DMSO-d$_6$) δ: 1.14-1.16 (1H, m), 1.17-1.19 (3H, m), 1.22-1.23 (2H, t), 1.39-1.43 (4H, t), 3.09-3.10 (2H, m), 3.53 (6H, s), 4.02-4.04 (1H, t), 6.15 (2H, s), 6.34 (1H, s), 6.98-7.00 (2H, dd), 7.18-7.20 (2H, dd), 7.22-7.27 (4H, m), 7.32-7.35 (1H, s), 7.45 (1H, s), 8.16-8.18 (1H, d), 8.90 (1H, s), 9.20 (1H, s), 10.73 (1H, s); m/z: (M + H)$^+$ at 593.2; pale yellow solid hygroscopic |
| 62 | 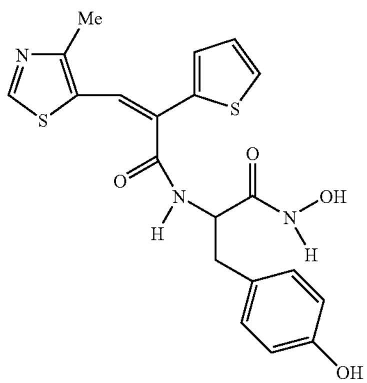 | $^1$H NMR (DMSO-d$_6$) δ: 2.50 (3H, s), 2.73-2.84 (2H, m), 4.40-4.43 (1H, t), 6.62-6.64 (2H, dd), 6.90-6.96 (3H, m), 7.19-7.20 (1H, m), 7.21-7.22 (1H, dd), 7.71 (1H, s), 7.80-7.82 (1H, d), 8.90 (2H, s), 9.20 (1H, s), 10.73 (1H, s); m/z: (M + H)$^+$ at 430.0; off white solid hygroscopic |
| 63 | 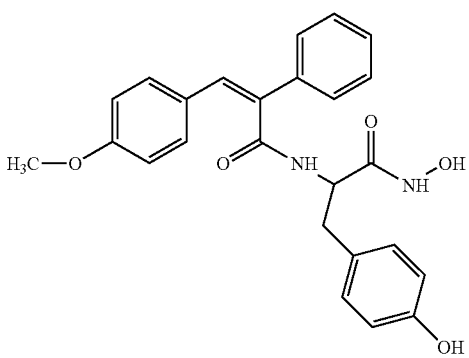 | $^1$H NMR (DMSO-d$_6$) δ: 2.88-2.93 (2H, m), 3.69 (3H, s) 4.54 (1H, t), 6.63-6.65 (2H, dd), 6.73-6.75 (2H, dd), 6.86-6.93 (4H, m), 7.07-7.08 (1H, m), 7.13-7.15 (1H, d), 7.40-7.41 (3H, d), 8.91 (2H, s), 9.22 (1H, s), 10.72 (1H, s); m/z: (M + H)$^+$ at 432.9; hygroscopic |
| 64 | 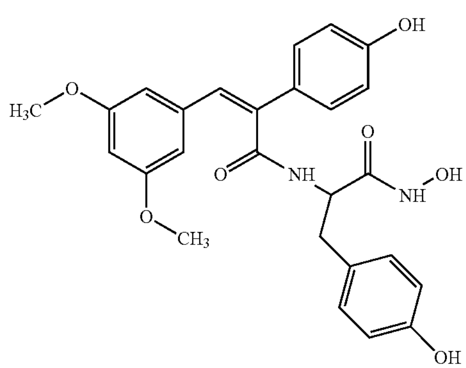 | $^1$H NMR (DMSO-d$_6$) δ: 2.86-2.91 (2H, m), 3.54 (6H, s) 4.56 (1H, t), 6.20-6.21 (2H, dd), 6.34 (1H, m), 6.63-6.65 (3H, m), 6.77-6.80 (2H, m), 6.86-6.89 (4H, m), 7.18/-7.20 (1H, d), 7.23 (1H, s), 9.26 (1H, s), 9.64 (1H, s); m/z: (M + H)$^+$ at 479.9; hygroscopic |

Anti-Cancer Experimental Methods

Anti-Cancer Screen:

Experimental drugs are screened for anti-cancer activity in three cell lines for their $GI_{50}$, TGI and $LC_{50}$ values (using five concentrations for each compound). The cell lines are maintained in DMEM containing 10% fetal bovine serum. 96 well micro titer plates are inoculated with cells in 100 µL for 24 h at 37° C., 5% CO2, 95% air and 100% relative humidity. 5000 HCT 116 cells/well, 5000 NCIH 460 cells/well and 5000 U251 cells/well are plated. A separate plate with these cell lines is also inoculated to determine cell viability before the addition of the compounds ($T_0$) (See Table I).

Addition of Experimental Drugs:

Following 24-hour incubation, experimental drugs are added to the 96 well plates. Each plate contains one of the above cell lines and the following in triplicate: five different concentrations (0.01, 0.1, 1, 10 and 100 µM) of four different compounds, appropriate dilutions of a cytotoxic standard and control (untreated) wells. Compounds are dissolved in DMSO to make 20 mM stock solutions on the day of drug addition and frozen at −20° C. Serial dilutions of these 20 mM stock solutions are made in complete growth medium such that 100 µL of these drug solutions in medium, of final concentrations equaling 0.01, 0.1, 1, 10 and 100 µM can be added to the cells in triplicate. Standard drugs whose anti-cancer activity has been well documented and which are regularly used are doxorubicin and SAHA. (See Table I).

End-Point Measurement:

For $T_0$ measurement, 24 hours after seeding the cells, 10 µL of 3-(4,5-Dimethyl-2-thiazolyl)-2,5-diphenyl-2H-tetrazolium (MTT) solution per well is added and incubation carried out for 3 hours at 37° C., 5% $CO_2$, 95% air and 100% relative humidity, protected from light. Cells incubated with compounds for 48 hours are treated similarly except with the addition of 20 µL MTT solution per well and a subsequent incubation under the same conditions. After 3 hours of MTT incubation, well contents are aspirated carefully followed by addition of 150 µL DMSO per well. Plates are agitated to ensure solution of the formazan crystals in DMSO and absorbance read at 570 nm. (See Table I).

Calculation of $GI_{50}$, TGI and $LC_{50}$:

Percent growth is calculated for each compound's concentration relative to the control and zero measurement wells ($T_0$; viability right before compound addition). If a test well's O.D. value is greater than the $T_0$ measurement for that cell line % Growth=(test−zero)/(control−zero)×100

If a test well's O.D. value is lower than the $T_0$ measurement for that cell line, then, % Growth=(test−zero)/zero×100

Plotting % growth versus experimental drug concentration, $GI_{50}$ is the concentration required to decrease % growth by 50%; TGI is the concentration required to decrease % growth by 100% and $LC_{50}$ is the concentration required to decrease % growth by 150%. (See Table I).

HDAC Activity Screening:

Histone Deacetylase (HDAC) Inhibition Assay using Boc-Lys (Ac)-AMC Substrate: Inhibition of HDAC has been implicated to modulate transcription and to induce apoptosis or differentiation in cancer cells. The fluorometric assay provides a fast and fluorescence based method that eliminates radioactivity, extractions or chromatography, as used in traditional assays. The assay based on two steps. First, the HDAC fluorometric substrate, which comprises an acetylated lysine side chain, is incubated with a sample containing HDAC activity (Mouse Liver Extract). Deacetylation of the substrate sensitizes the substrate, in the second step; treatment with the Trypsin stop solution produces a fluorophore that can be easily analyzed using fluorescence plate reader.

Assay was done in 96 well black microplate and total volume of the assay is 100 ul. Mouse liver enzyme is diluted 1:6 with HDAC buffer. Enzyme cocktail made of 10 ul of diluted enzyme and 30 ul of HDAC buffer. 40 ul of enzyme cocktail dispensed into each well. 10 ul of different concentrations of inhibitor added in to each well, except enzyme control well. Preincubated the plate at 30° C. for 5 minutes. The HDAC reaction is started by adding 50 ul of HDAC substrate (Boc-Lys (Ac)-AMC Substrate) solution. Incubated the plate at 30° C. for 30 minutes. Adding 100 ul of Trypsin stop solution stops the reaction. The plate is incubated again at 30° C. for 20-30 minutes. The release of AMC is monitored by measuring the fluorescence at excitation wavelength of 365 or 360 nm and emission wavelength of 440 or 460 nm. Buffer and substrate alone kept for blank subtraction. (Dennis Wegener et al, Anal. Biochem, 321, 2003, 202-208).

Results are indicated in the following Table I, wherein, (—Indicates Not Detected, and NA indicates Not Available)

TABLE I

| | NCIH460 | | | HCT116 | | | MDAMB231/U251 | | | Mean | HDAC Inhibition | | |
|---|---|---|---|---|---|---|---|---|---|---|---|---|---|
| S. No. | $GI_{50}$ | TGI | $LC_{50}$ | $GI_{50}$ | TGI | $LC_{50}$ | $GI_{50}$ | TGI | $LC_{50}$ | $GI_{50}$ | 1 µM | 10 µM | $IC_{50}$ µM |
| 1. | >100 | >100 | >100 | 5 | 15 | 70 | 0.1 | 34 | 75 | 2.6 | 53.76 | 66.42 | 0.22 |
| 2. | 27 | 40 | 56 | 30 | 53 | 73 | 30 | 97 | >100 | 29 | 7.73 | 10.46 | — |
| 3. | 50 | >100 | >100 | 40 | 72 | >100 | 73 | >100 | >100 | 54.3 | −6.41 | −6.45 | — |
| 4. | 45 | 77 | >100 | 9.4 | 44 | 80 | 55 | 75 | >100 | 36 | 16.9 | 24 | — |
| 5. | 50 | 75 | 100 | 35 | 62 | 90 | 65 | 80 | 92 | 50 | 19.6 | 35.3 | — |
| 6. | 44 | 74 | 85 | 38 | 65 | 91 | 60 | >100 | >100 | 47 | 15.9 | 36.1 | — |
| 7. | 0.01 | 0.03 | 10 | 0.98 | 1 | >100 | 0.8 | 39 | >100 | 0.6 | 7.3 | 3.8 | — |
| 8 | 15 | 62 | >100 | 8 | >100 | >100 | 6 | 32 | 96 | 9.7 | 77.63 | 99.67 | 0.55 |
| 9 | 45 | 73 | 100 | 20 | 58 | 95 | 28 | 58 | 90 | 31 | 65.5 | 98.28 | 0.7 |
| 13 | 7 | 42 | 75 | 5 | 35 | 70 | 3 | 38 | 80 | 5 | 53.83 | 89.18 | 2.95 |
| 14 | >100 | >100 | >100 | >100 | >100 | >100 | >100 | >100 | >100 | >100 | 21.1 | 35.4 | — |
| 15 | >100 | >100 | >100 | >100 | >100 | >100 | >100 | >100 | >100 | >100 | 1.7 | 4 | — |
| 16 | 0.01 | 0.03 | 24 | 1.9 | 2.5 | 32 | 0.15 | 27 | 90 | 0.7 | 68 | 83 | 0.061 |
| 17 | 0.25 | 0.7 | >100 | 0.03 | 1 | >100 | 0.71 | >100 | >100 | 0.3 | 0.7 | 2.3 | — |
| 18 | 0.5 | 60 | >100 | 55 | >100 | >100 | 0.8 | 1 | >100 | 18.8 | 2.26 | 0.89 | — |
| 19 | 8 | 68 | >100 | >100 | >100 | >100 | 5.8 | 9.2 | >100 | 6.9 | −22.2 | 10.2 | — |
| 20 | 1 | 82 | >100 | >100 | >100 | >100 | 3 | >100 | >100 | 2 | NA | 5.57 | — |
| 23 | 0.8 | 65 | >100 | 6 | 60 | >100 | 1 | 24 | 90 | 2.6 | 42.7 | 81.07 | 1.8 |
| 24 | 16 | 50 | 82 | 5 | 16 | >100 | 0.3 | 27 | 75 | 7.21 | 46.1 | 99.5 | — |
| 26 | 34 | 70 | >100 | 9 | 50 | 100 | 10 | 47 | 85 | 17.7 | 39.38 | 76.69 | — |

TABLE I-continued

| | NCIH460 | | | HCT116 | | | MDAMB231/U251 | | | Mean | HDAC Inhibition | | |
|---|---|---|---|---|---|---|---|---|---|---|---|---|---|
| S. No. | $GI_{50}$ | TGI | $LC_{50}$ | $GI_{50}$ | TGI | $LC_{50}$ | $GI_{50}$ | TGI | $LC_{50}$ | $GI_{50}$ | 1 μM | 10 μM | $IC_{50}$ μM |
| 27 | 30 | 64 | 96 | 7 | 41 | >100 | 7.5 | 42 | 82 | 14.8 | 37.49 | 73.77 | — |
| 28 | 9 | 42 | 82 | 5 | 9 | 45 | 4 | 20 | 100 | 6 | 70.82 | 90.20 | 0.44 |
| 29 | 28 | 66 | 89 | 5 | 44 | 78 | 6 | 45 | 90 | 13 | NA | NA | — |
| 30 | 30 | 80 | >100 | 6 | 45 | >100 | 3 | 42 | >100 | 13 | 52.95 | 84.69 | — |
| 31 | 9.7 | 70 | >100 | 5 | 9 | 97 | 6 | 22 | >100 | 6.9 | 72.20 | 91.49 | — |
| 36 | 2 | 9.5 | >100 | >100 | >100 | >100 | 0.2 | 98 | >100 | 1.1 | NA | NA | — |
| 37 | 26 | 58 | 90 | 6 | 19 | 90 | 5 | 32 | 80 | 12.3 | 56.87 | 83.89 | — |
| 38 | 6 | 20 | 64 | 5.5 | 15 | 65 | 0.07 | 4 | 60 | 3.9 | 59.26 | 97.74 | — |
| 40 | 3 | 30 | >100 | 5.8 | 23 | >100 | 1 | 8 | 80 | 3.27 | 79.97 | 96.16 | — |
| 41 | 15 | 55 | 94 | 6 | 32 | 90 | 9 | 46 | 90 | 10 | 68.69 | 92.83 | — |
| 43 | 10 | 62 | >100 | 5 | 9 | 70 | 0.05 | 5 | 75 | 5.017 | 89.26 | 100 | 0.26 |
| 45 | 16 | 57 | 89 | 6.8 | 25 | 73 | 5 | 45 | >100 | 9.3 | 60.17 | 95.83 | — |
| 46 | 5 | 53 | >100 | 7 | 45 | >100 | 3.5 | 34 | >100 | 5 | 60.53 | 70.82 | — |
| 47 | 13 | 55 | 98 | 9 | 50 | 95 | 7.5 | 48 | >100 | 9.8 | 49.92 | 87.19 | — |
| 51 | 30 | 80 | >100 | 10 | 65 | 84 | 9.6 | 35 | 86 | 16.5 | NA | NA | |
| 53 | 13 | 42 | 75 | 5 | 13 | 65 | 5 | 19 | 70 | 7.7 | 69.80 | 95.25 | 0.06 |

We claim:

1. A compound of formula (I),

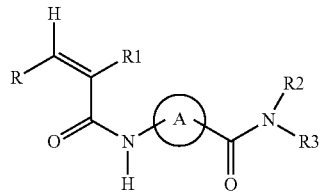

or a tautomeric form, a stereoisomer, pharmaceutically acceptable salt or composition thereof, wherein A represents $-(CH_2)_n$ which is optionally substituted or unsubstituted by groups selected from aryl, arylalkyl and heteroaryl, which are optionally substituted, the substituents being selected from hydroxy and halogen;

wherein R and $R_1$ represent aryl groups selected from the group consisting of phenyl and naphthyl which are optionally substituted; heteroaryl groups selected from the group consisting of pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl and pyridazinyl which are optionally substituted; or benzofused heteroaryl groups selected from the group consisting of quinoline, quinoxaline, acridine and phenazine which are optionally substituted;

n is an integer in the range of 1 to 8;

wherein when n is from 2 to 8, $R_2$ and $R_3$ represent hydrogen, hydroxyl, or substituted or unsubstituted groups selected from the group consisting of linear or branched ($C_1$-$C_4$) alkyl groups selected from the group consisting of methyl, ethyl, n-propyl, isopropyl, n-butyl, isobutyl and t-butyl; alkoxy groups selected from the group consisting of methoxy, ethoxy, propoxy, n-butoxy, isobutoxy and t-butoxy; benzyloxy; acetyl; benzyloxy acetyl; cycloalkyl groups selected from the group consisting of cyclohexyl, cycloheptyl and cyclooctyl; aryl groups selected from the group consisting of phenyl and naphthyl; heterocyclyl groups selected from the group consisting of pyrrolidinyl, thiazolidinyl, oxazolidinyl, morpholinyl, thiomorpholinyl, and piperazinyl; heteroaryl groups selected from the group consisting of pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl and pyridazinyl; and benzofused heteroaryl groups selected from the group consisting of quinoline, quinoxaline, acridine, phenazine and benzothiazole;

wherein when n is 1, $R_2$ and $R_3$ represent hydrogen, hydroxyl, or substituted or unsubstituted groups selected from the group consisting of: benzyloxy; acetyl; benzyloxy acetyl; cycloalkyl groups selected from the group consisting of cyclohexyl, cycloheptyl and cyclooctyl; aryl groups selected from the group consisting of phenyl and naphthyl; heteroaryl groups selected from the group consisting of pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl and pyridazinyl; and benzofused heteroaryl groups selected from the group consisting of quinoline, quinoxaline, acridine, phenazine and benzothiazole;

when the groups R, $R_1$, $R_2$ and $R_3$ are substituted, the substituents (which are one or more) are selected from the group consisting of halogens selected from the group consisting of fluorine, chlorine, bromine and iodine, hydroxy, nitro, cyano, azido, nitroso, amino, hydrazine, hydroxamate, formyl, alkyl, haloalkyl, haloalkoxy, cycloalkyl, aryl, benzyl, alkoxy, aryloxy, acyl, acyloxy, acyloxyacyl, heterocyclyl, heteroaryl, monoalkylamino, dialkylamino, acylamino, alkoxycarbonyl selected from the group consisting of methoxycarbonyl and ethoxycarbonyl, aryloxycarbonyl, alkylsulfonyl, arylsulfonyl, alkylsulfinyl, arylsulfinyl, thioalkyl, arylthio, sulfamoyl, alkoxyalkyl groups, carboxylic acid and carboxylic acid derivatives selected from the group consisting of esters, hydroxamic acid and hydroxamate, and wherein the substituents are further optionally substituted; and whenever the groups R, $R_1$, $R_2$ and $R_3$ represent substituted or unsubstituted 5 to 10 membered ring systems, the rings are monocyclic or bicyclic, saturated or partially saturated or aromatic containing 1 to 4 heteroatoms selected from the group consisting of O, S and N.

2. The pharmaceutical composition comprising a compound of formula (I) according to claim 1, as an active ingredient, along with a pharmaceutically acceptable carrier, diluent, or excipient.

3. The pharmaceutical composition according to claim 2, wherein the pharmaceutical composition is in a form of a tablet, capsule, powder, syrup, solution, aerosol or suspension.

4. The pharmaceutical composition according to claim 2, wherein the amount of the compound of formula (I) in the composition is less than 70% by weight.

5. A method of inhibiting HDAC in a cell comprising treating the cell with the compound according to claim 1.

6. A method for causing the regression of a condition mediated by HDAC selected from psoriasis, lung cancer, colon cancer, breast cancer and gliomas, comprising administering to a subject suffering from the condition mediated by HDAC the compound according to the claim 1.

7. A method of causing a regression of lung cancer, colon cancer, breast cancer and gliomas, comprising administering to a subject suffering from cancer the compound according to claim 1.

8. The compound of claim 1, selected from a group consisting of:

(2Z)-3-(3,5-Dimethoxyphenyl)-2-(4-fluorophenyl)-N-[6-{(2-hydroxyphenyl) amino}-6-oxohexyl]acrylamide;
(2Z)-3-(3,5-Dimethoxyphenyl)-2-(4-fluorophenyl)-N-[6-{(3-hydroxyphenyl) amino}-6-oxohexyl]acrylamide;
(2Z)-3-(3,5-Dimethoxyphenyl)-2-(4-fluorophenyl)-N-[6-(hydroxyamino)-6-oxo hexyl]acrylamide;
(2Z)-3-(3,5-Dimethoxyphenyl)-2-(4-hydroxyphenyl)-N46-{(2-aminophenyl)amino}6-oxo hexyl]acrylamide;
(2Z)-3-(3,5-Dimethoxyphenyl)-2-(4-hydroxyphenyl)-N-[6-{(2-hydroxyphenyl)amino}-6-oxohexyl]acrylamide;
(2Z)-3-(3,4,5-Trimethoxyphenyl)-2-(4-hydroxyphenyl)-N46-{(2-hydroxyphenyl)amino}-6-oxohexyl]acrylamide;
(2Z)-3-(3,4,5-Trimethoxyphenyl)-2-(4-hydroxyphenyl)-N-[6-(N,O dimethyl amine)-6-oxohexyl]acrylamide;
(2Z)-3-(4-Methyl-1,3-thiazol-5-yl)-2-(2-thienyl))-N-[6-(hydroxyamino)-6-oxohexyl]acrylamide;
(2Z)-3-(3,5-Dimethoxyphenyl)-2-(4-nitrophenyl)-N-[6-(hydroxyamino)-6-oxohexyl]acrylamide;
(2Z)-3-(3-Chloro-4-fluorophenyl)-2-(4-fluorophenyl)-N-[6-(hydroxyamino)-6-oxohexyl]acrylamide;
(2Z)-3-(3,5-Dimethoxyphenyl)-2-(4-hydroxyphenyl)-N-[6-(hydroxyamino)-6-oxohexyl]acrylamide;
(2Z)-3-(4-Methyl-1,3-thiazol-5-yl)-2-(4-chlorophenyl)-N-[6-(hydroxyamino)-6-oxohexyl]acrylamide;
(2Z)-3-(5-Bromo-2-thienyl)-2-(4-bromophenyl)-N-[6-(hydroxyamino)-6-oxohexyl]acrylamide;
(2Z)-3-(Pyridin-4-yl)-2-(4-fluorophenyl)-N-[6-(hydroxy amino)-6-oxo hexyl]acrylamide;
(2Z)-3-(Pyridin-4-yl)-2-(4-fluorophenyl)-N-[6-(4-hydroxy-2-nitrophenyl amine)-6-oxohexyl]acrylamide;
(2Z)-3-(4-Thiomethylphenyl)-2-(4-fluorophenyl)-N-[6-(hydroxyamine)-6-oxohexyl]acrylamide;
(2Z)-3-(4-Thiomethylphenyl)-2-(4-fluorophenyl)-N-[6-(5-nitro-2-thiazole amine)-6-oxohexyl]acrylamide;
(2Z)-3-(4-Thiomethylphenyl)-2-(4-fluorophenyl)-N-[6-(N,O dimethylamine)-6-oxohexyl]acrylamide;
(2Z)-3-(4-Thiomethylphenyl)-2-(4-fluorophenyl)-N-[6-(5-methyl-2-benzo thiazole amine)-6-oxohexyl]acrylamide;
(2Z)-3-(4-Thiomethylphenyl)-2-(4-fluorophenyl)-N-[6-(2-thiazoleamine)-6-oxohexyl]acrylamide;
(2Z)-3-(3,4-Difluorophenyl)-2-(4-fluorophenyl)-N-[6-(2-thiazoleamine)-6-oxohexyl]acrylamide;
(2Z)-3-(4-Fluoro-3-trifluoromethyl-phenyl)-2-(4-trifluoromethylphenyl)-N46-(hydroxyamino)-6-oxohexyl] acrylamide;
(2Z)-3-(4-Methylthiazol-5-yl)-2-(4-bromophenyl)-N-[6-(hydroxyamino)-6-oxohexyl]acrylamide;
(2Z)-3-(4-Fluoro-3-trifluoromethyl-phenyl)-2-(4-nitrophenyl)-N-[6-(hydroxyamino)-6-oxohexyl]acrylamide;
(2Z)-3-(2,3,5-Trifluoro-phenyl)-2-(thiophene-2-yl)-N-[6-(hydroxyamino)-6-oxohexyl]acrylamide;
(2Z)-3-(4-Methylthiazol-5-yl)-2-(4-trifluoromethylphenyl)-N46-(hydroxyamino)-6-oxohexyl]acrylamide;
(2Z)-3-(2,3,5-Trifluoro-phenyl)-2-(4-nitrophenyl)-N-[6-(hydroxyamino)-6-oxohexyl]acrylamide;
(2Z)-3-(3-Chlorophenyl)-2-(4-methoxyphenyl)-N-[6-(hydroxyamino)-6-oxohexyl]acrylamide;
(2Z)-3-(4-Methoxyphenyl)-2-(phenyl)-N-[6-(hydroxyamino)-6-oxohexyl]acrylamide;
(2Z)-3-(2-Nitrophenyl)-2-(4-chlorophenyl)-N-[6-(hydroxyamino)-6-oxohexyl]acrylamide;
(2Z)-3-(2-Chloro-4-fluorophenyl)-2-(phenyl)-N-[6-(hydroxyamino)-6-oxohexyl]acrylamide;
(2Z)-3-(3,4,5-Trimethoxyphenyl)-2-(4-hydroxyphenyl)-N—[O-benzyl-6-(hydroxyamino)-6-oxohexyl]acrylamide;
(2Z)-3-(3,5-Dimethoxyphenyl)-2-(4-fluorophenyl)-N—[O-benzyl-6-(hydroxyamino)-6-oxo hexyl]acrylamide;
(2Z)-3-(3,4-Difluorophenyl)-2-(4-fluorophenyl)-N-[6-(hydroxyamino)-6-oxohexyl]acrylamide;
(2Z)-3-(3,4-Difluorophenyl)-2-(4-fluorophenyl)-N-[6-(N,O dimethyl hydroxy amino-6-oxohexyl]acrylamide;
(2Z)-3-(5-Chloro-2-furyl)-2-(4-fluorophenyl)-N-[6-(hydroxyamino)-6-oxohexyl]acrylamide;
(2Z)-3-(4-Thiomethylphenyl)-2-(4-trifluoromethylphenyl)-N-[6-(hydroxyamino)-6-oxohexyl]acrylamide;
(2Z)-3-(Thiazol-2-yl)-2-(4-trifluoromethylphenyl)-N-[6-(hydroxyamino)-6-oxohexyl]acrylamide;
(2Z)-3-(2,3,6 Trifluorophenyl)-2-(4-methoxyphenyl)-N-[6-(hydroxyamino)-6-oxohexyl]acrylamide;
(2Z)-3-(4-Thiomethylphenyl)-2-(4-nitrophenyl)-N-[6-(hydroxyamino)-6-oxohexyl]acrylamide;
(2Z)-3-(3-Chloro-4-fluorophenyl)-2-(4-hydroxyphenyl)-N-[6-(hydroxyamino)-6-oxohexyl]acrylamide;
(2Z)-3-(4-Thiomethylphenyl)-2-(thiophene-2-yl)-N-[6-(hydroxyamino)-6-oxohexyl]acrylamide;
(2Z)-3-(5-Chlorothiophen-2-yl)-2-(4-fluorophenyl)-N-[6-(hydroxyamino)-6-oxohexyl]acrylamide;
(2Z)-3-(4-Fluoro-3-methylphenyl)-2-(4-fluorophenyl)-N-[6-(hydroxyamino)-6-oxohexyl]acrylamide;
(2Z)-3-(4-Hydroxy-3-methoxyphenyl)-2-(4-fluorophenyl)-N-[6-[(hydroxyamino)-6-oxohexyl]acrylamide;
(2Z)-3-(4-Trifluoromethylphenyl)-2-(4-fluorophenyl)-N-[6-(hydroxyamino)-6-oxohexyl]acrylamide;
(2Z)-3-(3,4,5-Trimethoxyphenyl)-2-(4 fluorophenyl)-N-[6-(hydroxyamino)-6-oxohexyl]acrylamide;
N-[4-(Hydroxyamino)-4-oxobutyl]-6-{[(2Z)-3-(3,5 dimethoxyphenyl)-2-(4 nitrophenyl)-acrylamide]}hexanamide;
(2Z)-3-(3,4,5-Trimethoxyphenyl)-2-(4-methoxyphenyl)-N-[6-(hydroxyamino)-6-oxohexyl]acrylamide;
(2Z)-3-(4-Thiomethylphenyl)-2-(4-fluorophenyl)-N-[6-(O-benzyl hydroxyamino)-6-oxohexyl]acrylamide;
N-Acetyl-6-{[(2Z)-3-(4-thiomethylphenyl)-2-(4-fluorophenyl)-acrylamide]}-N-hydroxyhexanamide;
N-Acetyl-6-{[(2Z)-3-(5-chloro-2-furyl)-2-(4-fluorophenyl)-acrylamide]}-N-hydroxyhexanamide;
N-Hydroxy-2-{[(2Z)-3-(4-thiomethylphenyl)-2-(4-fluorophenyl)-acrylamide]6-oxohexyl]amino}-3-(4-hydroxy phenyl)propanamide;

Methyl-2-{[(2Z)-3-(2,3,5,6 tetrafluoro-4-methoxyphenyl)-2-(4-fluorophenyl)-acryl amide]6-oxohexyl]amino}-3-(4-hydroxy phenyl)propanoate;

N-Hydroxy-2-{[(2Z)-2-(2,3,5,6 tetrafluoro-4-methoxyphenyl)-3-(4-fluorophenyl)-acrylamide]6-oxohexyl]amino}-3-(4-hydroxy phenyl)propanamide;

Methyl-2-{[(2Z)-2-(3,4 difluorophenyl)-3-(4-fluorophenyl)-acrylamide]6-oxohexyl]amino}-3-(4-hydroxy phenyl)propanoate;

N-Hydroxy-2-{[(2Z)-2-(3,4 difluorophenyl)-3-(4-fluorophenyl)-acrylamide]6-oxohexyl]amino}-3-(4-hydroxy phenyl)propanamide;

(2Z)—N-[2-(hydroxyamino)-1-(4-hydroxybenzyl)-2-oxoethyl]-3-(4-fluoro-3-trifluoromethyl phenyl)-2-(4-nitro phenyl)-acrylamide;

N-Hydroxy-2-{[(2Z)-3-(3,5 dimethoxyphenyl)-2-(4-fluorophenyl)-acrylamide]6-oxohexyl]amino}-3-(4-hydroxy phenyl)propanamide;

(2Z)—N-[2-(hydroxyamino)-1-(4-hydroxybenzyl)-2-oxoethyl]-3-(4-methyl thiazol-5-yl)-2-(thiophen-2-yl)-acrylamide;

(2Z)—N-[2-(hydroxyamino)-1-(4-hydroxybenzyl)-2-oxoethyl]-3-(4 methoxy phenyl)-2-(phenyl)-acrylamide; and (2Z)—N-[2-(hydroxyamino)-1-(4-hydroxybenzyl)-2-oxoethyl]-3-(3,5 dimethoxy phenyl)-2-(4-hydroxy phenyl)-acrylamide.

9. The compound of claim 1, selected from a group consisting of:

3-(3,5-Dimethoxyphenyl)-2-(4-fluorophenyl)-N46-(2-hydroxyphenyl)amino}-6-oxohexyl]acrylamide;

3-(3,5-Dimethoxyphenyl)-2-(4-fluorophenyl)-N-[6-{(3-hydroxyphenyl)amino}-6-oxohexyl]acrylamide;

3-(3,5-Dimethoxyphenyl)-2-(4-fluorophenyl)-N-[6-(hydroxyamino)-6-oxo hexyl]acrylamide;

3-(3,5-Dimethoxyphenyl)-2-(4-hydroxyphenyl)-N46-{(2-aminophenyl)amino}6-oxo hexyl]acrylamide;

3-(3,5-Dimethoxyphenyl)-2-(4-hydroxyphenyl)-N-[6-{(2-hydroxyphenyl)amino}-6-oxohexyl]acrylamide;

3-(3,4,5-Trimethoxyphenyl)-2-(4-hydroxyphenyl)-N-[6-{(2-hydroxyphenyl)amino-6-oxohexyl]acrylamide;

3-(3,4,5-Trimethoxyphenyl)-2-(4-hydroxyphenyl)-N-[6-(N,O dimethyl amine)-6-oxohexyl]acrylamide;

3-(4-Methyl-1,3-thiazol-5-yl)-2-(2-thienyl))-N-[6-(hydroxyamino)-6-oxohexyl]acrylamide;

3-(3,5-Dimethoxyphenyl)-2-(4-nitrophenyl)-N-[6-(hydroxyamino)-6-oxohexyl]acrylamide;

3-(3-Chloro-4-fluorophenyl)-2-(4-fluorophenyl)-N-[6-(hydroxyamino)-6-oxohexyl]acrylamide;

3-(3,5-Dimethoxyphenyl)-2-(4-hydroxyphenyl)-N-[6-(hydroxyamino)-6-oxohexyl]acrylamide;

3-(4-Methyl-1,3-thiazol-5-yl)-2-(4-chlorophenyl)-N-[6-(hydroxyamino)-6-oxohexyl]acrylamide;

3-(5-Bromo-2-thienyl)-2-(4-bromophenyl)-N-[6-(hydroxyamino)-6-oxohexyl]acrylamide;

3-(Pyridin-4-yl)-2-(4-fluorophenyl)-N-[6-(hydroxy amino)-6-oxo hexyl]acrylamide;

3-(Pyridin-4-yl)-2-(4-fluorophenyl)-N-[6-(4-hydroxy-2-nitrophenyl amine)-6-oxohexyl]acrylamide;

3-(4-Thiomethylphenyl)-2-(4-fluorophenyl)-N-[6-(hydroxyamine)-6-oxohexyl]acrylamide;

3-(4-Thiomethylphenyl)-2-(4-fluorophenyl)-N-[6-(5-nitro-2-thiazole amine)-6-oxohexyl]acrylamide;

3-(4-Thiomethylphenyl)-2-(4-fluorophenyl)-N-[6-(N,O dimethylamine)-6-oxohexyl]acrylamide;

3-(4-Thiomethylphenyl)-2-(4-fluorophenyl)-N-[6-(5-methyl-2-benzo thiazole amine)-6-oxohexyl]acrylamide;

3-(4-Thiomethylphenyl)-2-(4-fluorophenyl)-N-[6-(2-thiazoleamine)-6-oxohexyl]acrylamide;

3-(3,4-Difluorophenyl)-2-(4-fluorophenyl)-N-[6-(2-thiazoleamine)-6-oxohexyl]acrylamide;

3-(4-Fluoro-3-trifluoromethyl-phenyl)-2-(4-trifluoromethylphenyl)-N46-(hydroxyamino)-6-oxohexyl]acrylamide;

3-(4-Methylthiazol-5-yl)-2-(4-bromophenyl)-N-[6-(hydroxyamino)-6-oxohexyl]acrylamide;

3-(4-Fluoro-3-trifluoromethyl-phenyl)-2-(4-nitrophenyl)-N46-(hydroxyamino)-6-oxohexyl]acrylamide;

3-(2,3,5-Trifluoro-phenyl)-2-(thiophene-2-yl)-N-[6-(hydroxyamino)-6-oxohexyl]acrylamide;

3-(4-Methylthiazol-5-yl)-2-(4-trifluoromethylphenyl)-N-[6-(hydroxyamino)-6-oxohexyl]acrylamide;

3-(2,3,5-Trifluoro-phenyl)-2-(4-nitrophenyl)-N-[6-(hydroxyamino)-6-oxohexyl]acrylamide;

3-(3-Chlorophenyl)-2-(4-methoxyphenyl)-N-[6-(hydroxyamino)-6-oxohexyl]acrylamide;

3-(4-Methoxyphenyl)-2-(phenyl)-N-[6-(hydroxyamino)-6-oxohexyl]acrylamide;

3-(2-Nitrophenyl)-2-(4-chlorophenyl)-N-[6-(hydroxyamino)-6-oxohexyl]acrylamide;

3-(2-Chloro-4-fluorophenyl)-2-(phenyl)-N-[6-(hydroxyamino)-6-oxohexyl]acrylamide;

3-(3,4,5-Trimethoxyphenyl)-2-(4-hydroxyphenyl)-N—[O-benzyl-6-(hydroxyamino)-6-oxohexyl]acrylamide;

3-(3,5-Dimethoxyphenyl)-2-(4-fluorophenyl)-N—[O-benzyl-6-(hydroxyamino)-6-oxo hexyl]acrylamide;

3-(3,4-Difluorophenyl)-2-(4-fluorophenyl)-N-[6-(hydroxyamino)-6-oxohexyl]acrylamide;

3-(3,4-Difluorophenyl)-2-(4-fluorophenyl)-N-[6-(N,O dimethyl hydroxy amino)-6-oxohexyl]acrylamide;

3-(5-Chloro-2-furyl)-2-(4-fluorophenyl)-N-[6-(hydroxyamino)-6-oxohexyl]acrylamide;

3-(4-Thiomethylphenyl)-2-(4-trifluoromethylphenyl)-N-[6-(hydroxyamino)-6-oxohexyl]acrylamide;

3-(Thiazol-2-yl)-2-(4-trifluoromethylphenyl)-N-[6-(hydroxyamino)-6-oxohexyl]acrylamide;

3-(2,3,6 Trifluorophenyl)-2-(4-methoxyphenyl)-N-[6-(hydroxyamino)-6-oxohexyl]acrylamide;

3-(4-Thiomethylphenyl)-2-(4-nitrophenyl)-N-[6-(hydroxyamino)-6-oxohexyllacrylamide;

3-(3-Chloro-4-fluorophenyl)-2-(4-hydroxyphenyl)-N-[6-(hydroxyamino)-6-oxohexyl]acrylamide;

3-(4-Thiomethylphenyl)-2-(thiophene-2-yl)-N-[6-(hydroxyamino)-6-oxohexyl]acrylamide;

3-(5-Chlorothiophen-2-yl)-2-(4-fluorophenyl)-N-[6-(hydroxyamino)-6-oxohexyl]acrylamide;

3-(4-Fluoro-3-methylphenyl)-2-(4-fluorophenyl)-N-[6-(hydroxyamino)-6-oxohexyl]acrylamide;

3-(4-Hydroxy-3-methoxyphenyl)-2-(4-fluorophenyl)-N-[6-(hydroxyamino)-6-oxohexyl]acrylamide;

3-(4-Trifluoromethylphenyl)-2-(4-fluorophenyl)-N-[6-(hydroxyamino)-6-oxohexyl]acrylamide;

3-(3,4,5-Trimethoxyphenyl)-2-(4 fluorophenyl)-N-[6-(hydroxyamino)-6-oxohexyl]acrylamide;

N-[4-(Hydroxyamino)-4-oxobutyl]-6-{[3-(3,5 dimethoxyphenyl)-2-(4 nitrophenyl)-acrylamide]}hexanamide;

3-(3,4,5-Trimethoxyphenyl)-2-(4-methoxyphenyl)-N-[6-(hydroxyamino)-6-oxohexyl]acrylamide;

3-(4-Thiomethylphenyl)-2-(4-fluorophenyl)-N-[6-(O-benzyl hydroxyamino)-6-oxohexyl]acrylamide;

N-Acetyl-6-{[3-(4-thiomethylphenyl)-2-(4-fluorophenyl)-acrylamide]}-N-hydroxyhexanamide;

N-Acetyl-6-{[3-(5-chloro-2-furyl)-2-(4-fluorophenyl)-acrylamide]}-N-hydroxyhexanamide;

N-Hydroxy-2-{[3-(4-thiomethylphenyl)-2-(4-fluorophenyl)-acrylamide]6-oxohexyl]amino}-3-(4-hydroxy phenyl)propanamide;

Methyl-2-{[3-(2,3,5,6 tetrafluoro-4-methoxyphenyl)-2-(4-fluorophenyl)-acryl amide]6-oxohexyl]amino}-3-(4-hydroxy phenyl)propanoate;

N-Hydroxy-2-{[2-(2,3,5,6 tetrafluoro-4-methoxyphenyl)-3-(4-fluorophenyl)-acrylamide]6-oxohexyl]amino}-3-(4-hydroxy phenyl)propanamide;

Methyl-2-{[2-(3,4 difluorophenyl)-3-(4-fluorophenyl)-acrylamide]6-oxohexyl]amino}-3-(4-hydroxy phenyl) propanoate;

N-Hydroxy-2-{[(2Z)-2-(3,4 difluorophenyl)-3-(4-fluorophenyl)-acrylamide]6-oxohexyl]amino}-3-(4-hydroxy phenyl)propanamide;

N-[2-(hydroxyamino)-1-(4-hydroxybenzyl)-2-oxoethyl]-3-(4-fluoro-3-trifluoromethyl phenyl)-2-(4-nitro phenyl)-acrylamide;

N-Hydroxy-2-{[3-(3,5 dimethoxyphenyl)-2-(4-fluorophenyl)-acrylamide]6-oxohexyl]amino}-3-(4-hydroxy phenyl)propanamide;

N-[2-(hydroxyamino)-1-(4-hydroxybenzyl)-2-oxoethyl]-3-(4-methyl thiazol-5-yl)-2-(thiophen-2-yl)-acrylamide;

N-[2-(hydroxyamino)-1-(4-hydroxybenzyl)-2-oxoethyl]-3-(4 methoxy phenyl)-2-(phenyl)-acrylamide; and N-[2-(hydroxyamino)-1-(4-hydroxybenzyl)-2-oxoethyl]-3-(3,5 dimethoxy phenyl)-2-(4-hydroxy phenyl)-acrylamide.

10. A compound of formula (I),

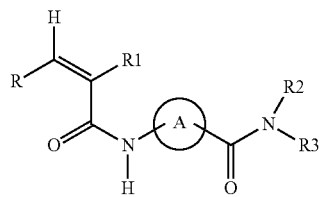

(I)

or a tautomeric form, a stereoisomer, a pharmaceutically acceptable salt or composition thereof, wherein A represents —(CH$_2$)$_n$ which is optionally substituted or unsubstituted by groups selected from aryl, arylalkyl and heteroaryl, which are optionally substituted, the substituents being selected from hydroxy and halogen;

wherein R and R$_1$ represent aryl groups which are optionally substituted; heteroaryl groups which are optionally substituted; or benzofused heteroaryl groups which are optionally substituted;

n is an integer in the range of 1 to 8;

wherein when n is from 2 to 8, R$_2$ and R$_3$ represent hydrogen, hydroxyl, or substituted or unsubstituted groups selected from the group consisting of: linear or branched (C$_1$-C$_4$) alkyl groups; benzyloxy; acetyl; benzyloxy acetyl; cycloalkyl groups; aryl groups; heterocyclyl groups except piperidinyl; heteroaryl groups; and benzofused heteroaryl groups;

wherein when n is 1, R$_2$ and R$_3$ represent hydrogen, hydroxyl, or substituted or unsubstituted groups selected from the group consisting of benzyloxy; acetyl; benzyloxy acetyl; cycloalkyl groups; aryl groups; heteroaryl groups; and benzofused heteroaryl groups;

when the groups R, R$_1$, R$_2$ and R$_3$ are substituted, the substituents (which are one or more) are selected from the group consisting of: halogens, hydroxy, nitro, cyano, azido, nitroso, amino, hydrazine, hydroxamate, formyl, alkyl, haloalkyl, haloalkoxy, cycloalkyl, aryl, benzyl, alkoxy, aryloxy, acyl, acyloxy, acyloxyacyl, heterocyclyl, heteroaryl, monoalkylamino, dialkylamino, acylamino, alkoxycarbonyl, aryloxycarbonyl, alkylsulfonyl, arylsulfonyl, alkylsulfinyl, arylsulfinyl, thioalkyl, arylthio, sulfamoyl, alkoxyalkyl groups, carboxylic acid and carboxylic acid derivatives, and wherein the substituents are further optionally substituted; and whenever the groups R, R$_1$, R$_2$ and R$_3$ represent substituted or unsubstituted 5 to 10 membered ring systems, the rings are monocyclic or bicyclic, saturated or partially saturated or aromatic containing 1 to 4 heteroatoms selected from the group consisting of O, S and N.

11. The pharmaceutical composition comprising a compound of formula (I) according to claim 10, as an active ingredient, along with a pharmaceutically acceptable carrier, diluent, or excipient-emote.

12. A method of causing a regression of diseases that are involved in cellular growth or a condition mediated by HDAC selected from lung cancer, colon cancer, breast cancer, gliomas and psoriasis, comprising administering the compound according to claim 10.

13. A method of inhibiting HDAC in a cell comprising treating the cell with the compound according to claim 10.

14. A method of causing a regression of lung cancer, colon cancer, breast cancer and gliomas comprising administering to a subject suffering from cancer the compound according to claim 10.

15. The compound according to claim 10, wherein the compound a compound of formula (I),

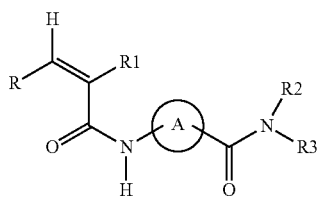

(I)

or a tautomeric form, a stereoisomer, a pharmaceutically acceptable salt or composition thereof, wherein A represents —(CH$_2$)$_n$ which is optionally substituted or unsubstituted by groups selected from aryl, arylalkyl and heteroaryl, which are optionally substituted, the substituents being selected from hydroxy and halogen;

wherein R and R$_1$ represent aryl groups which are optionally substituted; heteroaryl groups which are optionally substituted; or benzofused heteroaryl groups which are optionally or substituted;

wherein R$_2$ and R$_3$ represent hydrogen, hydroxyl, substituted or unsubstituted groups selected from the group consisting of: linear or branched (C$_1$-C$_4$) alkyl groups; benzyloxy; acetyl; benzyloxy acetyl; cycloalkyl groups; aryl groups; heterocyclyl groups except piperidinyl; heteroaryl groups; and benzofused heteroaryl groups;

n is an integer in the range of 2 to 8;

when the groups R, R$_1$, R$_2$ and R$_3$ are substituted, the substituents (which are one or more) are selected from the group consisting of: halogens, hydroxy, nitro, cyano, azido, nitroso, amino, hydrazine, hydroxamate, formyl, alkyl, haloalkyl, haloalkoxy, cycloalkyl, aryl, benzyl, alkoxy, aryloxy, acyl, acyloxy, acyloxyacyl, heterocyclyl, heteroaryl, monoalkylamino, dialkylamino, acylamino, alkoxycarbonyl, aryloxycarbonyl, alkylsulfonyl, arylsulfonyl, alkylsulfinyl, arylsulfinyl, thioalkyl, arylthio, sulfamoyl, alkoxyalkyl groups, carboxylic acid and carboxylic acid derivatives, and wherein the substituents are further optionally substituted; and whenever the groups R, $R_1$, $R_2$ and $R_3$ represent substituted or unsubstituted 5 to 10 membered ring systems, the rings are monocyclic or bicyclic, saturated or partially saturated or aromatic containing 1 to 4 heteroatoms selected from the group consisting of O, S and N.

16. A compound of formula (I),

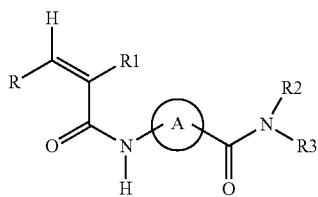

(I)

or a tautomeric form, a stereoisomer, a pharmaceutically acceptable salt and composition thereof, wherein A represents —$(CH_2)_n$;

wherein R and $R_1$ represent phenyl groups which are optionally substituted;

n is an integer in the range of 1 to 8;

wherein when n is from 2 to 8, $R_2$ and $R_3$ represent hydrogen, hydroxyl, or substituted or unsubstituted groups selected from the group consisting of: linear or branched ($C_1$-$C_4$) alkyl groups selected from the group consisting of methyl, ethyl, n-propyl, isopropyl, n-butyl, isobutyl and t-butyl; alkoxy groups selected from the group consisting of methoxy, ethoxy, propoxy, n-butoxy, isobutoxy and t-butoxy; benzyloxy; acetyl; benzyloxy acetyl; cycloalkyl groups selected from the group consisting of cyclohexyl, cycloheptyl and cyclooctyl; aryl groups selected from the group consisting of phenyl and naphthyl; heterocyclyl groups selected from the group consisting of pyrrolidinyl, thiazolidinyl, oxazolidinyl, morpholinyl, thiomorpholinyl, and piperazinyl; heteroaryl groups selected from the group consisting of pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl and pyridazinyl; and benzofused heteroaryl groups selected from the group consisting of quinoline, quinoxaline, acridine, phenazine and benzothiazole;

wherein when n is 1, one of $R_2$ or $R_3$ represent —$(CH_2)_3$CONHOH, and the other one of $R_2$ or $R_3$ represent hydrogen;

when the groups R, $R_1$, $R_2$ and $R_3$ are substituted, the substituents (which are one or more) are selected from the group consisting of: halogens selected from the group consisting of fluorine, chlorine, bromine and iodine, hydroxy, nitro, cyano, azido, nitroso, amino, hydrazine, hydroxamate, formyl, alkyl, haloalkyl, haloalkoxy, cycloalkyl, aryl, benzyl, alkoxy, aryloxy, acyl, acyloxy, acyloxyacyl, heterocyclyl, heteroaryl, monoalkylamino, dialkylamino, acylamino, alkoxycarbonyl selected from the group consisting of methoxycarbonyl and ethoxycarbonyl, aryloxycarbonyl, alkylsulfonyl, arylsulfonyl, alkylsulfinyl, arylsulfinyl, thioalkyl, arylthio, sulfamoyl, alkoxyalkyl groups, carboxylic acid and carboxylic acid derivatives selected from the group consisting of esters, hydroxamic acid and hydroxamate, and wherein the substituents are further optionally substituted; and whenever the groups R, $R_1$, $R_2$ and $R_3$ represent substituted or unsubstituted 5 to 10 membered ring systems, the rings are monocyclic or bicyclic, saturated or partially saturated or aromatic containing 1 to 4 heteroatoms selected from the group consisting of O, S and N.

17. The compound according to claim 16, wherein n is 1 and $R_2$ is —$(CH_2)_3$CONHOH and the compound is N-(1-(4-hydroxybenzyl)-2-{[4-(hydroxyamino)-4-oxobutyl]amino}-2-oxo ethyl)-3-(4-fluoro-3-trifluoro methyl phenyl)-2-(4-nitrophenyl)-acrylamide.

* * * * *

UNITED STATES PATENT AND TRADEMARK OFFICE
CERTIFICATE OF CORRECTION

PATENT NO.       : 8,263,044 B2
APPLICATION NO.  : 12/084430
DATED            : September 11, 2012
INVENTOR(S)      : Akella S. S. V. Srinivas et al.

It is certified that error appears in the above-identified patent and that said Letters Patent is hereby corrected as shown below:

In Col. 7, lines 58-59, "1. (2Z)-3-(3,5-Dimethoxyphenyl)-2-(4-fluorophenyl)-N-[6-(2-hydroxybenzyl amine)-6-oxohexyl]acrylamide;" should be --2. (2Z)-3-(3,5-Dimethoxyphenyl)-2-(4-fluorophenyl)-N-[6-{(2-hydroxyphenyl)amino}-6-oxohexyl]acrylamide;--.

In Col. 7, lines 60-61, "2. (2Z)-3-(3,5-Dimethoxyphenyl)-2-(4-fluorophenyl)-N-[6-(3-hydroxybenzyl amine)-6-oxohexyl]acrylamide;" should be --3. (2Z)-3-(3,5-Dimethoxyphenyl)-2-(4-fluorophenyl)-N-[6-{(3-hydroxyphenyl)amino}-6-oxohexyl]acrylamide;--.

In Col. 7, lines 62-63, "3. (2Z)-3-(3,5-Dimethoxyphenyl)-2-(4-fluorophenyl)-N-[6-(hydroxyamino)-6-oxo-hexyl]acrylamide;" should be --1. (2Z)-3-(3,5-Dimethoxyphenyl)-2-(4-fluorophenyl)-N-[6-(hydroxyamino)-6-oxo-hexyl]acrylamide;--.

In Col. 7, lines 64-65, "4. (2Z)-3-(3,5-Dimethoxyphenyl)-2-(4-hydroxyphenyl)-N-[6-(2-aminobenzyl amine)-6-oxohexyl]acrylamide;" should be --4. (2Z)-3-(3,5-Dimethoxyphenyl)-2-(4-hydroxyphenyl)-N-[6-{(2-aminophenyl)amino}-6-oxohexyl]acrylamide;--.

In Col. 7, lines 66-67, "5. (2Z)-3-(3,5-Dimethoxyphenyl)-2-(4-hydroxyphenyl)-N-[6-(2-hydroxybenzyl amine)-6-oxohexyl]acrylamide;" should be --5. (2Z)-3-(3,5-Dimethoxyphenyl)-2-(4-hydroxyphenyl)-N-[6-{(2-hydroxyphenyl)amino}-6-oxohexyl]acrylamide;--.

In Col. 8, lines 1-2, "6. (2Z)-3-(3,4,5-Trimethoxyphenyl)-2-(4-hydroxyphenyl)-N-[6-(2-hydroxybenzyl amine)-6-oxohexyl]acrylamide;" should be --6. (2Z)-3-(3,4,5-Trimethoxyphenyl)-2-(4-hydroxyphenyl)-N-[6-{(2-hydroxyphenyl)amino}-6-oxohexyl]acrylamide;--.

In Col. 8, lines 18-19, "14. (2Z)-3-(4-Pyridine)-2-(4-fluorophenyl)-N-[6-(hydroxyamino)-6-oxohexyl]acrylamide;" should be --14. (2Z)-3-(Pyridin-4-yl)-2-(4-fluorophenyl)-N-[6-(hydroxyamino)-6-oxohexyl]acrylamide;--.

Signed and Sealed this
Twelfth Day of February, 2013

Teresa Stanek Rea
*Acting Director of the United States Patent and Trademark Office*

CERTIFICATE OF CORRECTION (continued)

U.S. Pat. No. 8,263,044 B2

In Col. 8, lines 20-21, "15. (2Z)-3-(4-Pyridine)-2-(4-fluorophenyl)-N-[6-(4-hydroxy-2-nitrobenzylamine-)-6-oxohexyl]acrylamide;" should be --15. (2Z)-3-(Pyridin-4-yl)-2-(4-fluorophenyl)-N-[6-(4-hydroxy-2-nitrophenylamine)-6-oxohexyl]acrylamide;--.

In Col. 8, lines 56-57, "32. (2Z)-3-(2,3,4-Trimethoxyphenyl)-2-(4-hydroxyphenyl)-N-[6-(hydroxyamino)-6-oxohexyl]acrylamide;" should be --32. (2Z)-3-(3,4,5-Trimethoxyphenyl)-2-(4-hydroxyphenyl)-N-[6-(O-benzyl hydroxyamino)-6-oxohexyl]acrylamide;--.

In Col. 8, lines 58-59, "33. (2Z)-3-(3,5-Dimethoxyphenyl)-2-(4-fluorophenyl)-N-[6-(hydroxyamino)-6-oxohexyl]acrylamide;" should be --33. (2Z)-3-(3,5-Dimethoxyphenyl)-2-(4-fluorophenyl)-N-[6-(O-benzyl hydroxyamino)-6-oxohexyl]acrylamide;--.

In Col. 8, please delete lines 64-65.

In Col. 8, lines 66-67, "37." should be --36.--.

In Col. 9, line 1, "38." should be --37.--.

In Col. 9, line 3, "39." should be --38.--.

In Col. 9, line 5, "40." should be --39.--.

In Col. 9, line 7, "41." should be --40.--.

In Col. 9, line 9, "42." should be --41.--.

In Col. 9, line 11, "43." should be --42.--.

In Col. 9, line 13, "44." should be --43.--.

In Col. 9, line 15, "45." should be --44.--.

In Col. 9, line 17, "46." should be --45.--.

In Col. 9, line 19, "47." should be --46.--.

In Col. 9, line 21, "48." should be --47.--.

In Col. 9, lines 23-25, "49. N-[4-(hydroxyamino)-4-oxobutyl]-6-{[(2Z)-3-(3,5 dimethoxyphenyl)-2-(4 nitrophenyl)-acrylamide]}hexanamide;" should be --48. *N*-[4-(hydroxyamino)-4-oxobutyl]-6-{[(2Z)-3-(3,5 dimethoxyphenyl)-2-(4-nitrophenyl)-acrylamide]}hexanamide;--.

CERTIFICATE OF CORRECTION (continued)
U.S. Pat. No. 8,263,044 B2

In Col. 9, line 26, "50." should be --49.--.

In Col. 9, line 28, "51." should be --50.--.

In Col. 9, line 30, "52. N-Aetyl-6-{[(2Z)-3-(4-thiomethylphenyl)-2-(4-fluorophenyl)-acrylamide]}-N-hydroxyhexanamide;" should be --51. *N*-Acetyl-6-{[(2Z)-3-(4-thiomethylphenyl)-2-(4-fluorophenyl)-acrylamide]}-N-hydroxyhexanamide;--.

In Col. 9, line 32, "53. N-Acetyl-6-{[(2Z)-3-(5-chloro-2-furyl)-2-(4-fluorophenyl)-acrylamide]}-N-hydroxyhexanamide;" should be --52. *N*-Acetyl-6-{[(2Z)-3-(5-chloro-2-furyl)-2-(4-fluorophenyl)-acrylamide]}-N-hydroxyhexanamide;--.

In Col. 9, line 34, "54." should be --53.--.

In Col. 9, line 37, "55." should be --54.--.

In Col. 9, lines 40-42, "56. N-Hydroxy-2-{[(2Z)-3-(2,3,5,6 tetrafluoro-4-methoxyphenyl)-2-(4-fluoro phenyl)-acrylamide]6-oxohexyl]amino}-3-(4-hydroxyphenyl)propanamide;" should be --55. N-Hydroxy-2-{[(2Z)-2-(2,3,5,6 tetrafluoro-4-methoxyphenyl)-3-(4-fluorophenyl)-acrylamide]6-oxohexyl]amino}-3-(4-hydroxyphenyl)propanamide;--.

In Col. 9, lines 43-45, "57. Methyl-2-{[(2Z)-3-(3,4 difluorophenyl)-2-(4-fluorophenyl)-acrylamide]6-oxohexyl]amino}-3-(4-hydroxyphenyl)propanoate;" should be --56. Methyl-2-{[(2Z)-2-(3,4 difluorophenyl)-3-(4-fluorophenyl)-acrylamide]6-oxohexyl]amino}-3-(4-hydroxyphenyl) propanoate;--.

In Col. 9, lines 46-48, "58. N-hydroxy-2-{[(2Z)-3-(3,4 difluorophenyl)-2-(4-fluorophenyl)-acrylamide]6-oxohexyl]amino}-3-(4-hydroxyphenyl)propanamide;" should be --57. N-hydroxy-2-{[(2Z)-2-(3,4 difluorophenyl)-3-(4-fluorophenyl)-acrylamide]6-oxohexyl]amino}-3-(4-hydroxyphenyl)propanamide;--.

In Col. 9, lines 49-51, "59. (2Z)–N-(1-(4-hydroxybenzyl)-2-{[4-(hydroxyamino)-4-oxobutyl]amino}-2-oxoethyl)-3-(4-fluoro-3-trifluoro methylphenyl)-2-(4-nitrophenyl)-acrylamide;" should be --58. (2Z)-*N*-(1-(4-hydroxybenzyl)-2-{[4-(hydroxyamino)-4-oxobutyl]amino}-2-oxoethyl)-3-(4-fluoro-3-trifluoromethylphenyl)-2-(4-nitrophenyl)-acrylamide;--.

In Col. 9, lines 52-54, "60. (2Z)–N-(2-(hydroxyamino)-1-(4-hydroxybenzyl)-2-oxoethyl]-3-(4-fluoro-3-trifluoromethylphenyl)-2-(4-nitrophenyl)-acrylamide;" should be --59. (2Z)-*N*-[2-(hydroxyamino)-1-(4-hydroxybenzyl)-2-oxoethyl]-3-(4-fluoro-3-trifluoromethylphenyl)-2-(4-nitrophenyl)-acrylamide;--.

CERTIFICATE OF CORRECTION (continued)

In Col. 9, lines 55-57, "61. N-Hydroxy-2-{[(2Z)-3-(3,4 dimethoxyphenyl)-2-(4-fluorophenyl)-acrylamide]6-oxohexyl]amino}-3-(4-hydroxyphenyl)propanamide;" should be --60. N-Hydroxy-2-{[(2Z)-3-{3,5 dimethoxyphenyl)-2-(4-fluorophenyl)-acrylamide]6-oxohexyl]amino}-3-(4-hydroxyphenyl)propanamide;--.

In Col. 9, lines 58-60, "62. (2Z)–N-[2-(hydroxyamino)-1-(4-hydroxybenzyl)-2-oxoethyl]-3-(4-methyl thiazol-5-yl)-2-(thiophen-2-yl)-acrylamide;" should be --61. (2Z)-*N*-[2-(hydroxyamino)-1-(4-hydroxybenzyl)-2-oxoethyl]-3-(4-methyl thiazol-5-yl)-2-(thiophen-2-yl)-acrylamide--.

In Col. 9, lines 61-62, "63. (2Z)–N-[2-(Hydroxyamino)-1-(4-hydroxybenzyl)-2-oxoethyl]-3-(4 methoxy phenyl)-2-(phenyl)-acrylamide;" should be --62. (2Z)-*N*-[2-(Hydroxyamino)-1-(4-hydroxybenzyl)-2-oxoethyl]-3-(4 methoxy phenyl)-2-(phenyl)-acrylamide; and--.

In Col. 9, lines 63-65, "64. (2Z)–N-[2-(hydroxyamino)-1-(4-hydroxybenzyl)-2-oxoethyl]-3-(3,5 dimethoxyphenyl)-2-(4-hydroxyphenyl)-acrylamide and" should be --63. (2Z)-*N*-[2-(hydroxyamino)-1-(4-hydroxybenzyl)-2-oxoethyl]-3-(3,5 dimethoxyphenyl)-2-(4-hydroxyphenyl)-acrylamide.--.

In Col. 23, the formula of Exp. 21 should be shown as:

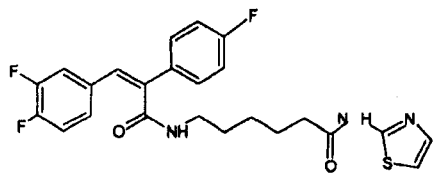

In Col. 27, the formula of Exp. 36 should be shown as:

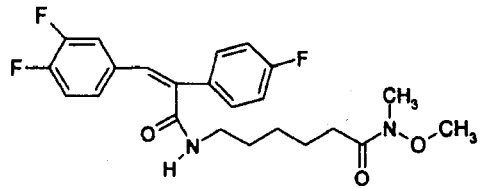

In Col. 27, Exp. "36" should be --35--.

In Col. 27, Exp. "37" should be --36--.

In Col. 27, Exp. "38" should be --37--.

In Col. 27, Exp. "39" should be --38--.

In Col. 29, Exp. "40" should be --39--.

In Col. 29, Exp. "41" should be --40--.

In Col. 29, Exp. "42" should be --41--.

In Col. 29, Exp. "43" should be --42--.

In Col. 29, Exp. "44" should be --43--.

In Col. 29, Exp. "45" should be --44--.

In Col. 31, Exp. "46" should be --45--.

In Col. 31, Exp. "47" should be --46--.

In Col. 31, Exp. "48" should be --47--.

In Col. 31, Exp. "49" should be --48--.

In Col. 31, Exp. "50" should be --49--.

In Col. 31, Exp. "51" should be --50--.

In Col. 33, line 1, "EXAMPLE 52" should be --EXAMPLE 51--.

In Col. 33, Exp. "53" should be --52--.

In Col. 34, line 1, "EXAMPLE 54" should be --EXAMPLE 53--.

In Col. 35, Exp. "55" should be --54--.

In Col. 35, Exp. "56" should be --55--.

In Col. 37, Exp. "57" should be --56--.

In Col. 37, Exp. "58" should be --57--.

In Col. 37, Exp. "59" should be --58--.

In Col. 37, Exp. "60" should be --59--.

In Col. 39, Exp. "61" should be --60--.

In Col. 39, Exp. "62" should be --61--.

In Col. 39, Exp. "63" should be --62--.

In Col. 39, Exp. "64" should be --63--.

In Col. 50, line 22, "or excipient-emote" should be --or excipient.--.

In Col. 50, line 34, "compound a compound of formula (I)," should be --compound is a compound of formula (I),--.

In Col. 50, line 56, "optionally or substituted;" should be --optionally substituted--.

In Col. 50, lines 57-58, "wherein $R_2$ and $R_3$ represent hydrogen, hydroxyl, substituted" should be --wherein $R_2$ and $R_3$ represent hydrogen, hydroxyl or substituted--.